(12) United States Patent
Morgan et al.

(10) Patent No.: US 9,532,827 B2
(45) Date of Patent: Jan. 3, 2017

(54) CONNECTION OF A BIPOLAR ELECTROSURGICAL HAND PIECE TO A MONOPOLAR OUTPUT OF AN ELECTROSURGICAL GENERATOR

(75) Inventors: Roy E. Morgan, Alameda, CA (US); Wayne K. Auge, II, Santa Fe, NM (US)

(73) Assignee: NuOrtho Surgical Inc., Fall River, MA (US)

(*) Notice: Subject to any disclaimer, the term of this patent is extended or adjusted under 35 U.S.C. 154(b) by 403 days.

(21) Appl. No.: 13/335,674

(22) Filed: Dec. 22, 2011

(65) Prior Publication Data
US 2012/0095457 A1 Apr. 19, 2012

Related U.S. Application Data

(63) Continuation-in-part of application No. 12/486,616, filed on Jun. 17, 2009.

(60) Provisional application No. 61/446,468, filed on Feb. 24, 2011.

(51) Int. Cl.
*A61B 18/12* (2006.01)
*A61B 18/14* (2006.01)
*A61B 18/16* (2006.01)
*A61B 18/00* (2006.01)

(52) U.S. Cl.
CPC ........ *A61B 18/1233* (2013.01); *A61B 18/1206* (2013.01); *A61B 18/148* (2013.01); *A61B 18/16* (2013.01); *A61B 2018/0091* (2013.01); *A61B 2018/00589* (2013.01); *A61B 2018/00601* (2013.01); *A61B 2018/00875* (2013.01)

(58) Field of Classification Search
CPC ................. A61B 2018/1253; A61B 2018/126; A61B 18/12; A61B 18/1206; A61B 2018/1246; A61B 18/1233
USPC ..................................................... 606/34–38
See application file for complete search history.

(56) References Cited

U.S. PATENT DOCUMENTS

| | | |
|---|---|---|
| 3,903,891 A | 9/1975 | Brayshaw |
| 3,911,107 A | 10/1975 | Krezanoski |
| 3,941,135 A | 3/1976 | von Sturm |
| 3,982,017 A | 9/1976 | Thiele |
| 4,014,777 A | 3/1977 | Brown |
| 4,060,088 A | 11/1977 | Morrison et al. |
| 4,094,320 A | 6/1978 | Newton |

(Continued)

FOREIGN PATENT DOCUMENTS

| | | |
|---|---|---|
| GB | 2037920 | 7/1980 |
| WO | 96/00042 | 1/1996 |

(Continued)

OTHER PUBLICATIONS

Babincova, Melania et al., "High-Gradient Magnetic Capture of Ferrofluids: Implications for Drug Targeting and Tumor Embolization", Zeitschrift fur Naturforschung vol. 56-C, 2001, 909-911.

(Continued)

*Primary Examiner* — Jaymi Della
(74) *Attorney, Agent, or Firm* — Peacock Myers, P.C.; Janeen Vilven; Deborah Peacock

(57) ABSTRACT

A method and apparatus for operatively connecting a bipolar electrosurgical hand piece to a monopolar output of an electrosurgical unit wherein active components simulate expected impedance characteristics of monopolar return electrodes connected to a patient.

6 Claims, 19 Drawing Sheets

(56) References Cited

U.S. PATENT DOCUMENTS

| | | |
|---|---|---|
| 4,105,017 A | 8/1978 | Ryaby |
| 4,231,372 A | 11/1980 | Newton |
| 4,237,887 A | 12/1980 | Gonser |
| 4,266,532 A | 5/1981 | Ryaby |
| 4,266,533 A | 5/1981 | Ryaby |
| 4,343,308 A | 8/1982 | Gross |
| 4,416,277 A | 11/1983 | Newton et al. |
| 4,504,493 A | 3/1985 | Marshall et al. |
| 4,540,409 A | 9/1985 | Nystrom et al. |
| 4,559,036 A | 12/1985 | Wunsch |
| 4,615,347 A | 10/1986 | Schooley |
| 4,827,927 A | 5/1989 | Newton |
| 4,872,865 A | 10/1989 | Bloebaum et al. |
| 4,901,719 A | 2/1990 | Trenconsky et al. |
| 4,938,970 A | 7/1990 | Hustead et al. |
| 4,971,068 A | 11/1990 | Sahi |
| 5,014,699 A | 5/1991 | Pollack et al. |
| 5,236,456 A | 8/1993 | O'Leary et al. |
| 5,282,861 A | 2/1994 | Kaplan |
| 5,304,724 A | 4/1994 | Newton |
| 5,314,476 A | 5/1994 | Prewett et al. |
| 5,342,357 A | 8/1994 | Nardella |
| 5,352,463 A | 10/1994 | Badylak et al. |
| 5,360,440 A | 11/1994 | Andersen |
| 5,364,395 A | 11/1994 | West, Jr. et al. |
| 5,366,443 A | 11/1994 | Eggers et al. |
| 5,403,825 A | 4/1995 | Lagarde et al. |
| 5,458,596 A | 10/1995 | Lax et al. |
| 5,472,442 A | 12/1995 | Klicek |
| 5,494,538 A | 2/1996 | Kirillov et al. |
| 5,498,259 A | 3/1996 | Mourant et al. |
| 5,514,130 A | 5/1996 | Baker |
| 5,516,533 A | 5/1996 | Badylak et al. |
| 5,554,141 A | 9/1996 | Wendler |
| 5,569,241 A | 10/1996 | Edwards |
| 5,569,242 A | 10/1996 | Lax et al. |
| 5,573,424 A * | 11/1996 | Poppe ............... 439/502 |
| 5,584,863 A | 12/1996 | Rauch et al. |
| 5,622,725 A | 4/1997 | Kross |
| 5,633,578 A | 5/1997 | Eggers et al. |
| 5,669,904 A | 9/1997 | Platt et al. |
| 5,669,907 A | 9/1997 | Platt et al. |
| 5,669,934 A | 9/1997 | Sawyer |
| 5,683,366 A | 11/1997 | Eggers et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,741,261 A | 4/1998 | Moskovitz et al. |
| 5,746,896 A | 5/1998 | Shimamune et al. |
| 5,749,895 A | 5/1998 | Sawyer et al. |
| 5,772,659 A | 6/1998 | Becker et al. |
| 5,788,976 A | 8/1998 | Bradford |
| 5,797,902 A | 8/1998 | Netherly |
| 5,800,385 A | 9/1998 | Demopulos et al. |
| 5,820,583 A | 10/1998 | Demopulos et al. |
| 5,824,015 A | 10/1998 | Sawyer |
| 5,840,166 A | 11/1998 | Kaneko |
| 5,855,608 A | 1/1999 | Brekke |
| 5,860,950 A | 1/1999 | Demopulos et al. |
| 5,871,469 A | 2/1999 | Eggers et al. |
| 5,885,277 A | 3/1999 | Korth |
| 5,885,292 A | 3/1999 | Moskovitz et al. |
| 5,891,140 A | 4/1999 | Ginn et al. |
| 5,919,191 A | 7/1999 | Lennox et al. |
| 5,955,514 A | 9/1999 | Huang et al. |
| 5,964,968 A | 10/1999 | Kaneko |
| 6,007,532 A | 12/1999 | Netherly |
| 6,032,077 A | 2/2000 | Pomeranz |
| 6,033,654 A | 3/2000 | Stedronsky et al. |
| 6,056,746 A | 5/2000 | Goble et al. |
| 6,068,627 A | 5/2000 | Orszulak et al. |
| 6,086,585 A | 7/2000 | Hovda et al. |
| 6,093,186 A | 7/2000 | Goble |
| 6,112,122 A | 8/2000 | Schwardt et al. |
| 6,113,596 A | 9/2000 | Hooven et al. |
| 6,117,109 A | 9/2000 | Eggers et al. |
| 6,135,998 A | 10/2000 | Palanker |
| 6,142,992 A | 11/2000 | Cheng et al. |
| 6,149,620 A | 11/2000 | Baker et al. |
| 6,159,194 A | 12/2000 | Eggers et al. |
| 6,162,219 A | 12/2000 | Nilsson et al. |
| 6,174,309 B1 | 1/2001 | Wrublewski et al. |
| 6,203,541 B1 | 3/2001 | Keppel |
| 6,206,875 B1 | 3/2001 | Long et al. |
| 6,206,878 B1 | 3/2001 | Bishop et al. |
| 6,207,134 B1 | 3/2001 | Fahlvik et al. |
| 6,210,403 B1 | 4/2001 | Klicek et al. |
| 6,213,999 B1 | 4/2001 | Platt et al. |
| 6,214,003 B1 | 4/2001 | Morgan et al. |
| 6,224,592 B1 | 5/2001 | Eggers et al. |
| 6,235,024 B1 | 5/2001 | Tu |
| 6,241,723 B1 | 6/2001 | Heim et al. |
| 6,241,753 B1 | 6/2001 | Knowlton |
| 6,261,286 B1 | 7/2001 | Goble et al. |
| 6,264,650 B1 | 7/2001 | Hovda et al. |
| 6,264,652 B1 | 7/2001 | Eggers et al. |
| 6,273,883 B1 | 8/2001 | Furumoto |
| 6,293,942 B1 | 9/2001 | Goble et al. |
| 6,296,636 B1 | 10/2001 | Cheng et al. |
| 6,306,134 B1 | 10/2001 | Goble et al. |
| 6,309,387 B1 | 10/2001 | Eggers et al. |
| 6,322,549 B1 | 11/2001 | Eggers et al. |
| 6,325,799 B1 | 12/2001 | Goble |
| 6,350,276 B1 | 2/2002 | Knowlton |
| 6,371,967 B1 | 4/2002 | Long et al. |
| 6,383,184 B1 | 5/2002 | Sharkey |
| 6,391,025 B1 | 5/2002 | Weinstein et al. |
| 6,416,509 B1 | 7/2002 | Goble et al. |
| 6,419,815 B1 | 7/2002 | Chambers et al. |
| 6,442,418 B1 | 8/2002 | Evans et al. |
| 6,461,352 B2 | 10/2002 | Morgan et al. |
| 6,463,336 B1 | 10/2002 | Mawhinney |
| 6,471,993 B1 | 10/2002 | Shastri et al. |
| 6,547,794 B2 | 4/2003 | Auge |
| 6,558,382 B2 | 5/2003 | Jahns et al. |
| 6,743,248 B2 | 6/2004 | Edwards et al. |
| 6,772,013 B1 | 8/2004 | Ingle et al. |
| 6,780,178 B2 | 8/2004 | Palanker et al. |
| 6,824,555 B1 | 11/2004 | Towler et al. |
| 6,832,995 B1 | 12/2004 | Towler et al. |
| 6,890,332 B2 | 5/2005 | Truckai et al. |
| 6,902,564 B2 | 6/2005 | Morgan et al. |
| 7,004,939 B2 | 2/2006 | Mackay |
| 7,066,932 B1 | 6/2006 | Morgan et al. |
| 7,105,011 B2 | 9/2006 | Auge |
| 7,131,860 B2 | 11/2006 | Sartor et al. |
| 7,137,980 B2 | 11/2006 | Buysse et al. |
| 7,160,293 B2 | 1/2007 | Sturm et al. |
| 7,300,435 B2 | 11/2007 | Wham et al. |
| 7,354,438 B2 | 4/2008 | Morgan et al. |
| 7,367,976 B2 | 5/2008 | Lawes et al. |
| 7,393,354 B2 | 7/2008 | Buchman et al. |
| 7,416,437 B2 | 8/2008 | Sartor et al. |
| 7,438,714 B2 | 10/2008 | Phan |
| 7,445,619 B2 | 11/2008 | Auge et al. |
| 7,481,810 B2 | 1/2009 | Drumbauld et al. |
| 7,549,989 B2 | 6/2009 | Morgan et al. |
| 7,713,269 B2 | 5/2010 | Auge et al. |
| 7,771,422 B2 | 8/2010 | Auge et al. |
| 7,819,861 B2 | 10/2010 | Auge et al. |
| 7,819,864 B2 | 10/2010 | Morgan et al. |
| 7,879,034 B2 | 2/2011 | Woloszko et al. |
| 7,955,296 B1 | 6/2011 | Morgan et al. |
| 8,235,979 B2 | 8/2012 | Morgan et al. |
| 8,361,065 B2 | 1/2013 | West, Jr. |
| 8,591,508 B2 | 11/2013 | Morgan et al. |
| 8,623,012 B2 | 1/2014 | Morgan et al. |
| 8,734,441 B2 | 5/2014 | Morgan et al. |
| 2001/0007940 A1 | 7/2001 | Tu et al. |
| 2001/0039419 A1 | 11/2001 | Francischelli et al. |
| 2002/0165596 A1 | 11/2002 | Wilson |
| 2002/0183737 A1 | 12/2002 | Kristensen |
| 2003/0028189 A1 | 2/2003 | Woloszko |

(56) References Cited

U.S. PATENT DOCUMENTS

| | | |
|---|---|---|
| 2003/0036753 A1 | 2/2003 | Morgan et al. |
| 2003/0216732 A1 | 11/2003 | Truckai et al. |
| 2003/0216733 A1 | 11/2003 | McClurken et al. |
| 2004/0030330 A1* | 2/2004 | Brassell et al. ............. 606/41 |
| 2004/0082945 A1 | 4/2004 | Clague et al. |
| 2004/0082946 A1 | 4/2004 | Malis et al. |
| 2004/0167244 A1 | 8/2004 | Auge, II |
| 2004/0267255 A1 | 12/2004 | Auge, II et al. |
| 2005/0015085 A1* | 1/2005 | McClurken et al. ........... 606/45 |
| 2005/0085806 A1 | 4/2005 | Auge, II et al. |
| 2005/0182449 A1 | 8/2005 | Auge et al. |
| 2005/0283151 A1 | 12/2005 | Ebbutt et al. |
| 2006/0079873 A1 | 4/2006 | Scopton et al. |
| 2006/0210552 A1 | 9/2006 | Demopulos et al. |
| 2007/0016182 A1 | 1/2007 | Lipson et al. |
| 2008/0281316 A1 | 11/2008 | Carlton et al. |
| 2008/0287948 A1 | 11/2008 | Newton et al. |
| 2009/0030410 A1 | 1/2009 | Auge, II et al. |
| 2009/0306645 A1 | 12/2009 | Morgan et al. |
| 2010/0069975 A1 | 3/2010 | Auge et al. |
| 2010/0087815 A1 | 4/2010 | Morgan et al. |
| 2010/0262136 A1 | 10/2010 | Morgan |
| 2011/0034914 A1 | 2/2011 | Auge et al. |
| 2011/0087308 A1 | 4/2011 | Morgan et al. |
| 2011/0196366 A1 | 8/2011 | Humble |
| 2013/0060249 A1 | 3/2013 | Maeda et al. |

FOREIGN PATENT DOCUMENTS

| | | |
|---|---|---|
| WO | WO02/102438 | 12/2002 |
| WO | WO03/015865 | 2/2003 |
| WO | WO-03103522 | 6/2003 |
| WO | WO-03/103521 | 12/2003 |
| WO | 2011/047148 | 4/2011 |
| WO | WO-2011047148 | 4/2011 |

OTHER PUBLICATIONS

Brennetot, R. et al., "Investigation of Chelate Formation, Intramoecular Energy Transfer and Luminescence Efficiency and Lifetimes in the Euthenoyltrifluoroacetone-trioctylphosphine oxide-Triton x-100 System Using Absorbance, Fluorescence and Photothermal Measurements", Spectrochim ACTA A Mol. Biomol. Spectrosc., Part A-56, 2000, 702-715.

Chen, S. S. et al., "Heat-Induced Changes in the Mechanics of a Collagenous Tissue: Isothermal, Isotonic Shrinkage", Transactions of the ASME vol. 120, 1998, 382-388.

Edwards, R B. et al., "Thermometric determination of cartilage matrix temperatures during thermal chondroplasty: comparison of bipolar and monopolar radiofrequency devices", Arthroscopy Apr. 2002;18(4), Apr. 2002, 339-346.

Fink, Bernd et al., "Holmium: YAG Laser-Induced Aseptic Bone Necroses of the Femoral Condyle", Arthroscopy: The Journal of Arthroscopic and Related Surgery vol. 12 No. 2, 1996, 217-223.

Gould, Stephen E. et al., "Cellular Contribution of Bone Graft to Fusion", Journal of Orthopaedic Research vol. 18, 2000, 920-927.

Grant, Kyle M. et al., "Magnetic Field-Controlled Microfluidic Transport", Journal of American Chemical Society (JACS) Articles, vol. 124, No. 3, 2002, 462-467.

Auge, "Redox Magnetohydrodynamic Engineered Irrigants Are Based Upon Constituent Charege-to-mass Ratio Profiles", 6th Annual Conference on the Physics, Chemistry, and Biology of Water, Oct. 20, 2011.

Ganguly, et al., "Nanomedical DNA Conduction: Accessing Genomic Control Mechanisms Associated with Biosynthetic Tissue Assembly", Ninth International Nanomedicine and Drug Delivery Symposium, Oct. 15, 2011, 1-5.

Ito, et al., "Sensitivity of Osteoinductive Activity of Deminerlization and Defatted Rat Femur to Temperature and Duration of Heating", Clinical Orthopaedics and Related Research No. 316, 1995, 267-275.

Janzen, et al., "Osteonecrosis After Contact Neodymium: Yttrium Aluminum Garnet Arthroscopic Laser Meniscectomy", AJR 169, 1997, 855-858.

Lopez, et al., "Effects of Monopolar Radiofrequency Energy on Ovine Joint Capsular Mechanical Properties", Clinical Orthopaedics and Related Research, No. 374, 2000, 286-297.

Medvecky, et al., "Thermal Capsular Shrinkage: Basic Science and Clinical Applications", Arthroscopy vol. 17 No. 6, 2001, 624-635.

Millenbaugh, et al., "Gene Expression Changes in the Skin of Rats Induced by Prolonged 35 GHz Millimeter-Wave Exposure", Radiation Research vol. 169 No. 3, 2010, 288-300.

Minczykowski, et al., "Effects of Magnetic Resonance Imaging on Polymorphonuclear Neutrophil Adhesion", Diagnostics and Medical Technology, Medical Science Monitor vol. 7 No. 3, 2001, 482-488.

Rozbruch, et al., "Osteonecrosis of the Knee Following Arthroscopic Laser Meniscectomy", Arthroscopy: The Journal of Arthroscopic and Related Surgery vol. 12 No. 2, 1996, 245-250.

Thal, et al., "Delayed Articular Cartilage Slough: Two Cases Resulting From Holmium: YAG Laser Damage to Normal Articular Cartilage and a Review of the Literature", Arthroscopy: The Journal of Arthroscopic and Related Surgery vol. 12 No. 1, 1996, 92-94.

Torchilin, et al., "Drug Targeting", European Journal of Pharmaceutical Sciences 11 Suppl 2, 2000, S81-S91.

Wall, et al., "Thermal Modification of Collagen", J. Shoulder Elbow Surg. vol. 8 No. 4, 1999, 339-344.

Wallace, et al., "Electrothermal Shrinkage Reduces Laxity but Alters Creep Behavior in a Lapine Ligament Model", J. Shoulder Elbow Surg. vol. 10 No. 1, 2001, 1-6.

Weston, et al., "Redox-Magnetohydrodynamic Microfluids Without Cannels and Compatible with Electrochemical Detection Under Immunoassay Conditions", Analytical Chemistry vol. 87 No. 17, 2010, 7068-7072.

Zhang, et al., "Effect(s) of the Demineralization Process on the Osteoinductivity of Demineralization Bone Matrix", J. Periodontol vol. 68, No. 11, 1997, 1085-1092.

Zohar, et al., "Thermal Imaging of Receptor-Activated Heat Production in Single Cells", Biophysical Journal vol. 74, 1998, 82-89.

Mourant, et al., "Improvements in Laser "Welding" of Chicken Bone Tibias in vitro", Proc. SPIE 2395, Lasers in Surgery: Advanced Characterization, Therapeutics, and Systems V, 478; doi:10.1117/12.209134, 1995, 1-8.

Mourant, et al., "Laser Welding of Bone: Successful in vitro Experiments", Proc. SPIE 2128, Laser Surgery: Advanced Characterization, Therapeutics, and Systems IV, 484, doi:10.1117/12.184934, 1994, 1-5.

* cited by examiner

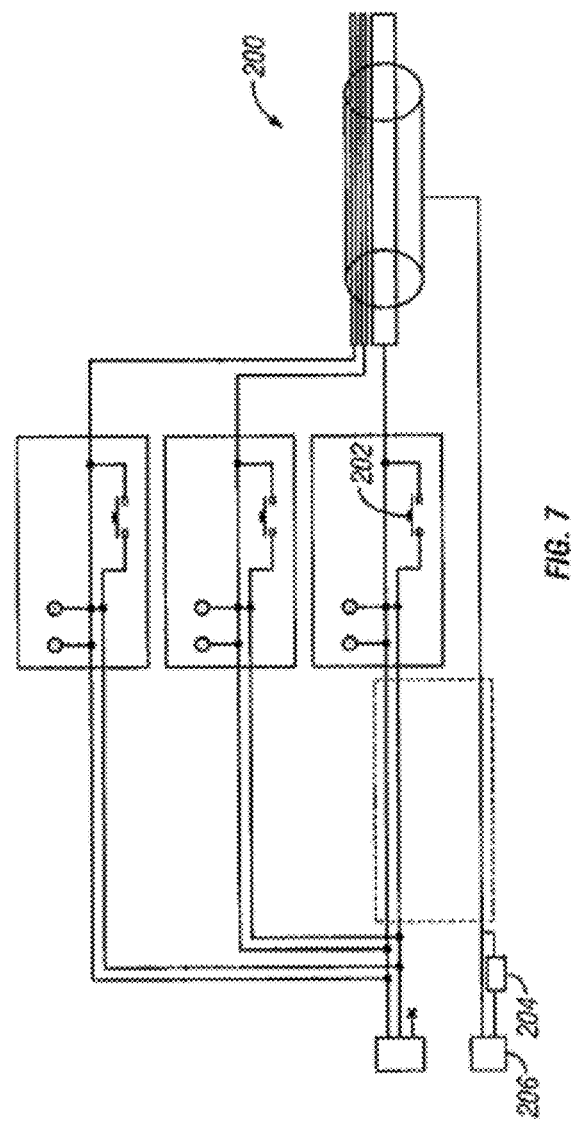

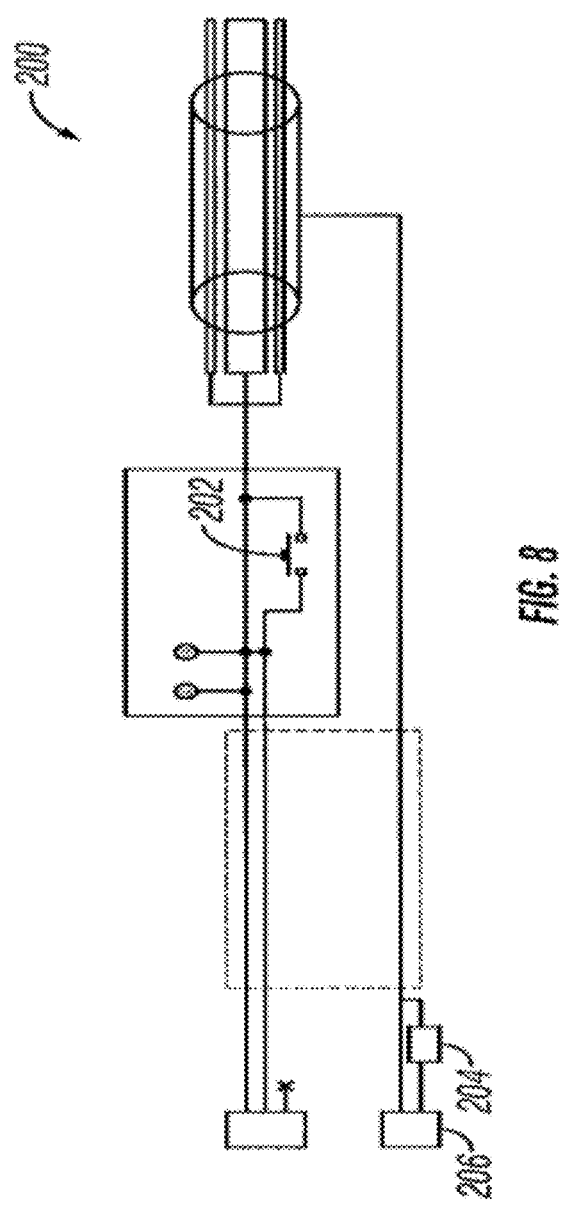

| ConMed *System 5000*™ | | | |
|---|---|---|---|
| Modes Available | General | | |
| | Fluids | | |
| | Laparoscopic | | |
| COAG - Output Signal Modifiers | Spray | Standard | Pinpoint |
| Output Choke Mode – Known as "Pulse" mode output (works with "Spray" & "Standard" Signals ONLY across all output modes) | Yes | Yes | No |

Fig. 11

| Capacitance (μF) | Rating (Vdc-Max) | Effect | Notes / Comments | Configuration Across R.P. Terminals |
|---|---|---|---|---|
| 0.01 | 400 | Out of Range | Impedance too low for recognition | single ceramic cap across terminals |
| 0.011 | 50 | Out of Range | Impedance too low for recognition | two 0.022uF, Poly caps in series |
| 0.022 | 50 | Out of Range | Impedance too low for recognition | single ceramic cap across terminals |
| 0.05 | 50 | In-Range | 1 out of 8 bars intermittently on Recognition monitor | two 0.1uF, 50Vdc ceramic caps in Series |
| 0.067 | 50 | In-Range | 4 out of 8 Bars on Recognition monitor | one 0.1uF, 50Vdc Met-film cap in series with one 0.22uF poly cap |
| 0.1 | 50 | In-Range | 5 out of 8 Bars on Recognition monitor | Single ceramic or poly Cap across terminals |
| 0.11 | 50 | In-Range | 6 out of 8 Bars on Recognition monitor | two 0.22μF, 50Vdc poly caps in series |
| 0.2 | 50 | In-Range | 7 out of 8 Bars on Recognition monitor | two 0.1uF, 50Vdc Poly caps in Parallel |
| 0.3 | 50 | In-Range | 8 out of 8 Bars on Recognition monitor | three (3)- 0.1uF, 50Vdc (2)poly caps and (1) ceramic Cap in Parallel |
| 0.44 | 50 | In-Range | Produces single panel R.P. Green Monitor | two 0.22uF, 50Vdc poly caps in parallel |
| 1.49 | 50 | In-Range | Produces single panel R.P. Green Monitor | Two series Aluminum Cap (1-4.7uF; 1-2.2uF) across terminals |
| 2.2 | 50 | In-Range | Produces single panel R.P. Green Monitor | Single Aluminum Electrolytic Cap across terminals |
| 4.7 | 50 | In-Range | Produces single panel R.P. Green Monitor | Single Aluminum Electrolytic Cap across terminals |
| 22 | 25 | In-Range | Produces single panel R.P. Green Monitor | Single Aluminum Electrolytic Cap across terminals |
| 68 | 16 | In-Range | Produces single panel R.P. Green Monitor | Single Aluminum Electrolytic Cap across terminals |
| 100 | 16 | In-Range | Produces single panel R.P. Green Monitor | Single Aluminum Electrolytic Cap across terminals |
| | Notes: | | | |
| | 1 | | For production getting close to 0.1uF can be done with a series wiring of 0.22uF ceramic caps across the R.P. Terminals. | |
| | 2 | | For production getting close to 0.2uF can be done with a series wiring of 0.47uF ceramic capsacross the R.P. Terminals. | |

Fig. 12

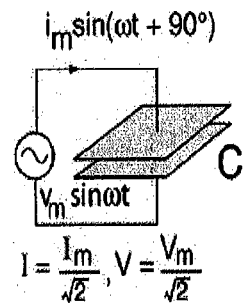

Fig. 13A

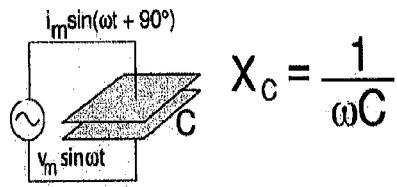

Fig. 13B

| Capacitance (µF) | Rating (Vdc-Max) | Effect | Notes / Comments | Configuration Across R.P. Terminals |
|---|---|---|---|---|
| 0.067 | 50 | In-Range | 4 out of 8 Bars on Recognition monitor | one 0.1uF, 50Vdc Met-film cap in series with one 0.22uF poly cap |
| 0.1 | 50 | In-Range | 5 out of 8 Bars on Recognition monitor | Single ceramic or poly Cap across terminals |
| 0.11 | 50 | In-Range | 6 out of 8 Bars on Recognition monitor | two 0.22µF, 50Vdc poly caps in series |
| 0.2 | 50 | In-Range | 7 out of 8 Bars on Recognition monitor | two 0.1uF, 50Vdc Poly caps in Parallel |
| 0.3 | 50 | In-Range | 8 out of 8 Bars on Recognition monitor | three (3)- 0.1uF, 50Vdc (2)poly caps and (1) ceramic Cap in Parallel |
| | Notes: | | | |
| | 1 | | For production getting close to 0.1uF can be done with a series wiring of 0.22uF ceramic caps across the R.P. Terminals. | |
| | 2 | | For production getting close to 0.2uF can be done with a series wiring of 0.47uF ceramic caps across the R.P. Terminals. | |

Fig. 14

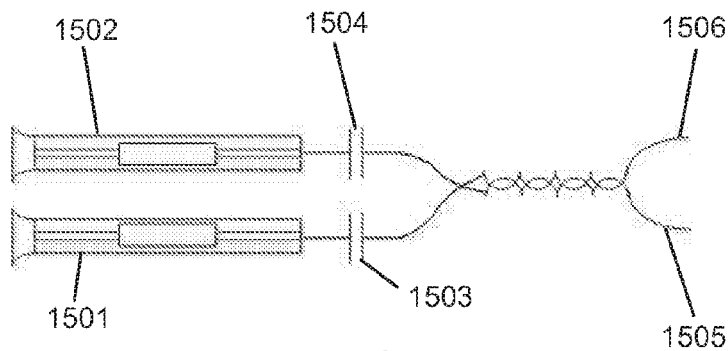

FIG. 15

| Criteria / Requirement | Capacitor Value / Part No | | Comments / Notes |
| --- | --- | --- | --- |
| | 0.22μF | 0.033μF | |
| Form-factor < 4.5mm dia. X 5.5mm length | Y | Y | Both have similar F.F. = (2.54mm x 4.32mm) / (3.05mm x 4.32mm) Respectively |
| Form-factor = axial | Y | Y | |
| Tolerance rating = ±20% or better (smaller) | Y | Y | 0.22μF Available in both tolerances / 0.033μF only in 20% |
| Voltage raging = 50Vdc or better (higher) | Y | Y | 50V only |
| Shall withstand 30min continuous activation w/o dielectric breakdown or overheating (45°C max.) | ? | ? | Presently unknown. |
| Capacitors shall be readily available from more than a single source supplier | Y | Y | Both available from Kemet and AVX |

FIG. 16

CONNECTION OF A BIPOLAR ELECTROSURGICAL HAND PIECE TO A MONOPOLAR OUTPUT OF AN ELECTROSURGICAL GENERATOR

CROSS-REFERENCE TO RELATED APPLICATIONS

This application claims priority to and the benefit of the filing of U.S. Provisional Patent Application Ser. No. 61/446,468, entitled "Modification of the Device Considering the Electrosurgical Generator", filed on Feb. 24, 2011, and the specification thereof is incorporated herein by reference. This application is also a Continuation-In-Part patent application of U.S. patent application Ser. No. 12/486,616, entitled "Active Conversion of a Monopolar Circuit to a Bipolar Circuit Using Impedance Feedback Balancing", filed on Jun. 17, 2009, and the specification and claims thereof is also incorporated herein by reference.

BACKGROUND OF THE INVENTION

1. Field of the Invention (Technical Field)

Embodiments of the present invention relate to the general field of electrosurgical generators that are used to power devices, such as instrument probes, developed for use in surgical and medical procedures.

2. Description of Related Art

The use of electrosurgical instruments in various types of surgical procedures has become widespread and generally consists of a system whereby a treatment device probe is connected to an electrosurgical generator. The device probe delivers the energy from the electrosurgical generator to the tissue treatment site via electrodes to provide a therapeutic effect. Device probe and electrosurgical generator architecture have been developed for particular therapeutic needs, depending upon, for example, the goals of treatment, the tissue type to be treated, and the treatment environment. Most commonly, electrosurgical generators consist of either monopolar or bipolar configurations, or both, which have become well known in the art. Likewise, either monopolar or bipolar treatment device probes have been developed to connect to those types of electrosurgical generators via an electrosurgical generator output port, either monopolar or bipolar, respectively. Active (or working) and return (reference) electrodes then function in a variety of ways based upon, for example, configuration, architecture, and connection to the electrosurgical generator. In this manner, either a monopolar or bipolar output portal, or both, exists on the electrosurgical generator into which the device probe, either a monopolar or bipolar device respectively, is connected. A monopolar device is connected to a monopolar output portal on the electrosurgical generator and, likewise, a bipolar device is connected to a bipolar output portal on the electrosurgical generator. Typically, feedback from the treatment site is then managed by way of the relevant monopolar or bipolar circuitry within the electrosurgical generator and between the device probe electrodes that are connected to the electrosurgical generator accordingly.

More generally, and to date, the electrosurgical industry has provided a wide variety of products geared toward this single-mode of operation from specific electrosurgical generator output portals (monopolar or bipolar). Within this design limitation, specific control mechanisms, circuitry, and software algorithms have been developed and applied to the management of the variable feedback that can be obtained from a single portal output for any given device.

Since device probe geometries tend to be more fixed than variable with respect to monopolar or bipolar configuration, the electrical signature of a given device is commonly treated as a constant within the context of an overall surgical procedure; i.e. a monopolar or a bipolar device.

The direct result of this prior art has been to provide specific output portals for the most common types of electrosurgery; those being monopolar and bipolar. Each of these output portals is designed to provide specific controls that limit the amount of maximum current, voltage or time-based modulations of current and voltage in response to the variations in factors at the treatment site. The result is intended to control the overall output to the active (working) end of the attached device probe and keep its general state of operation within a specified "safe-range" to avoid excessive heat, current, or current density from forming within the surgical site or elsewhere within the patient at the time of treatment.

Such circuitry for this monopolar or bipolar configured output portals is contained within the physical confines of the electrosurgical generator enclosure itself, proximal to the connection of the device probe, and is coupled to an electronic and software controller that monitors said variables and continually checks their time-varying values against preset performance limits. When these performance limits are exceeded, the controlling algorithm forces a safety trip, thus shutting down the primary RF-power output to the working end of the attached device. The specifics of these predefined software controlled trip points is that they are based on the electro physical constraints electrosurgical generator manufacturers have placed on the output portals, which as previously discussed, are configuration specific (monopolar or bipolar). Thus, the physical spacing of primary components such as the active (working) and return (reference) electrodes plays a paramount role in what those specific characteristics are that govern said trip points for safety control.

The overall industry result from this configuration model is a trajectory of "silo" thinking for each specific electrosurgical output portal, meaning that devices have been optimized for either the monopolar output portal or bipolar output portal of electrosurgical generators. Traditional thinking of the prior art has been that there is no advantage in shrinking the physical space of a given portals output for a specific mode, meaning that a monopolar procedure that involves a separated ground pad, typically placed at a great distance from the surgical site, has been thought to need such separation to operate effectively and that such separation is exactly why the procedure has been named "mono" polar as the electrical poles are separated by such large relative distances that only a single pole is effectively at work within the surgical site. On the other end of the spectrum is the "bi" polar method of electrosurgery which has drawn its name from the physical basis of active (working) and return (reference) electrode proximities to one and other. Thus, to date industry has remained ensconced in fixed paradigm of one treatment device probe configuration per output port of the electrosurgical generator; i.e. monopolar device to monopolar output port and bipolar device to bipolar output port.

BRIEF SUMMARY OF THE INVENTION

An embodiment of the present invention relates to an electronic bridging circuit which includes one or more circuit components arranged in electrical communication with a primary radiofrequency active or reference/return electrode lead of a hand piece of an electrosurgical generator upon which lead a super-imposed rider wave signal is transmitted, the super-imposed wave signal normalized to a monopolar balanced state of feedback to the electrosurgical generator reference plate electrode monitoring circuit via the one or more circuit components; the one or more circuit components selected to affect the super-imposed wave signal by balancing the rider signal; and wherein monopolar outputs of the electrosurgical generator are converted to bipolar outputs compatible with the hand piece upon connection of hand piece with the generator. In the circuit, a plurality of the circuit components can be connected in a parallel configuration, a series configuration, or a combination thereof. The circuit components can include a capacitor, an inductor, a resistor or pluralities and/or combinations thereof. If a capacitor is provided, it can optionally have a value of about 1 picofarad to a value of about 1 microfarad, more preferably about 40 picofarads to a value of about 0.1 microfarad. Optionally, one or more of the components can be arranged in a bridge circuit.

An embodiment of the present invention also relates to an electrosurgical apparatus comprising a conventionally-shaped monopolar output universal plug for the delivery of primary RF electrical current, which comprises no more than two of the typical three conductors.

An embodiment of the present invention also relates to a method for converting a monopolar electrosurgical generator which outputs a power wave and a super-imposed rider wave for use in a bipolar electrosurgical configuration which method includes bridging leads connected to the monopolar electrosurgical generator with a bridging circuit having at least one balancing component, the balancing component selected such that the impedance encountered by the rider wave when traveling through a bipolar hand piece and the balancing component is substantially similar to the impedance encountered by the rider wave when a monopolar hand piece and return pad is connected to the electrosurgical generator. The balancing component can be disposed within the bipolar hand piece. The balancing component can comprise a plurality of components which can be active, resistive, or a combination thereof. The bipolar hand piece can be electrically connected to only one of the cut or coagulate outputs of the monopolar electrosurgical generator.

An embodiment of the present invention also relates to a method for using a monopolar output of an electrosurgical generator for a bipolar electrosurgical application which method includes connecting a plurality of active electrodes of a bipolar electrosurgical hand piece to an active electrode port of a monopolar electrosurgical generator; providing one or more components through which a reference signal passes, the one or more components selected such that the total impendence encountered by the reference signal is at least substantially similar to a total impedance which would be encountered by the reference signal if it were traveling through a functioning monopolar electrosurgical hand piece. At least one of the plurality of active electrodes can be connected to the active electrode port of the monopolar electrosurgical generator through a switch. Optionally, each of a plurality of the active electrodes can be connected to the active electrode port of the monopolar electrosurgical generator through respective switches. The plurality of active electrodes can be individually and/or simultaneously activated.

An embodiment of the present invention relates to an electrosurgical apparatus which includes a monopolar electrosurgical generator connected to a bipolar electrosurgical hand piece. The hand piece can operate in a cut only mode or in a coagulate only mode.

An embodiment of the present invention also relates to a bipolar electrosurgical hand piece connectable and operable with a monopolar electrosurgical generator.

In an alternative embodiment, the electrosurgical hand piece of each of the foregoing embodiments can be operable in-situ and optionally with a liquid environment about a tip of the hand piece.

An embodiment of the present invention also relates to a bipolar electrosurgical hand piece having a housing for a connector of an monopolar electrosurgical hand piece, a pair of active electrical components disposed within the housing, the components at least substantially mimicking a load response produced by an external return circuit of a monopolar electrosurgical unit; and the bipolar electrosurgical hand piece connected to the connector and operably connectable to monopolar outputs of a monopolar electrosurgical unit. Optionally, the pair of active electrical components can be a pair of capacitors, which can optionally be at least substantially matching capacitors, each of which can be formed from at least two capacitors arranged in series, parallel, and/or a combination of series and parallel. Optionally, a monopolar electrosurgical generator can be connected to the bipolar electrosurgical hand piece.

An embodiment of the present invention also relates to a method for operably connecting a bipolar electrosurgical hand piece to a monopolar electrosurgical generator, which can include electrically connecting a first active electrical component from a first return port of the generator to a first conductor of a probe-tip of the hand piece; electrically connecting a second active electrical component from a second return port of the generator to the first conductor of the prop-tip of the hand piece; connecting a primary power output of the generator and the common output of the generator to a second conductor of the probe-tip of the hand piece.

Optionally the first active electrical component and the second active electrical component can comprise electrical characteristics which are substantial similar to one another. The first active electrical component and the second active electrical component can include a plurality of active components, which can optionally include capacitors. Optionally, the first and second active electrical components can each comprise a single capacitor or can each comprise a plurality of capacitors. Optionally, one or more of the capacitors can have a value of from about 0.05 µF to about 0.5 µF, more preferably about 0.1 µF to about 0.33 µF. Optionally, at least one of the active components can be disposed at least substantially within a connector. In one embodiment, the method can include electrically connecting non-active electrical components to the first conductor of the probe-tip of the hand piece. Optionally, the first conductor of the probe-tip can include a return electrode of the hand piece. Alternatively, the first conductor of the probe-tip can include an active electrode of the probe-tip of the hand piece.

An embodiment of the present invention also relates to an adaptor that includes inputs which at least substantially mate with one or more monopolar outputs of an electrosurgical generator; outputs which at least substantially mate with a bipolar electrosurgical hand piece; and one or more active electrical components connected such that when the generator is powering a bipolar hand piece from the generator's monopolar output, a return signal observed by the generator is substantially similar to a return signal formed when the generator is powering a monopolar hand piece from the generator's monopolar output. The return signal from the bipolar hand piece can fall within a predetermined range of return signals that the generator regards as acceptable.

Aspects, advantages and novel features, and further scope of applicability of embodiments of the present invention will be set forth in part in the detailed description to follow, taken in conjunction with the accompanying drawings, and in part will become apparent to those aspects and advantages of embodiments of the present invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 7 is a drawing which schematically illustrates an embodiment of the present invention wherein a plurality of electrodes are connected to a plurality of switches;

FIG. 8 is a drawing which schematically illustrates an embodiment of the present invention wherein a plurality of active electrodes are connected to a single switch;

FIG. 11 is a table which illustrates information regarding an ESU;

FIG. 12 is a table which illustrates test results of various capacitor values being placed across electrode terminals of an ESU;

FIGS. 13A and 13B illustrate a schematic of an alternating current source connected to a capacitor and the equation for current flow through the capacitor, the equation for voltage drop across a capacitor; and the impedance of a capacitor;

FIG. 14 is a table which illustrates a results of an experiment wherein various capacitor values where arranged in parallel in the circuit of FIG. 9B and the effects thereof were monitored as a number of bars of recognition on the ESU;

FIG. 15 illustrates an arrangement for a pair of capacitors according to an embodiment of the present invention;

FIG. 16 is a table which illustrates a comparison of attributes of a 0.22 µF capacitor and a 0.33 µF capacitor;

DETAILED DESCRIPTION OF THE INVENTION

Figure 1A:
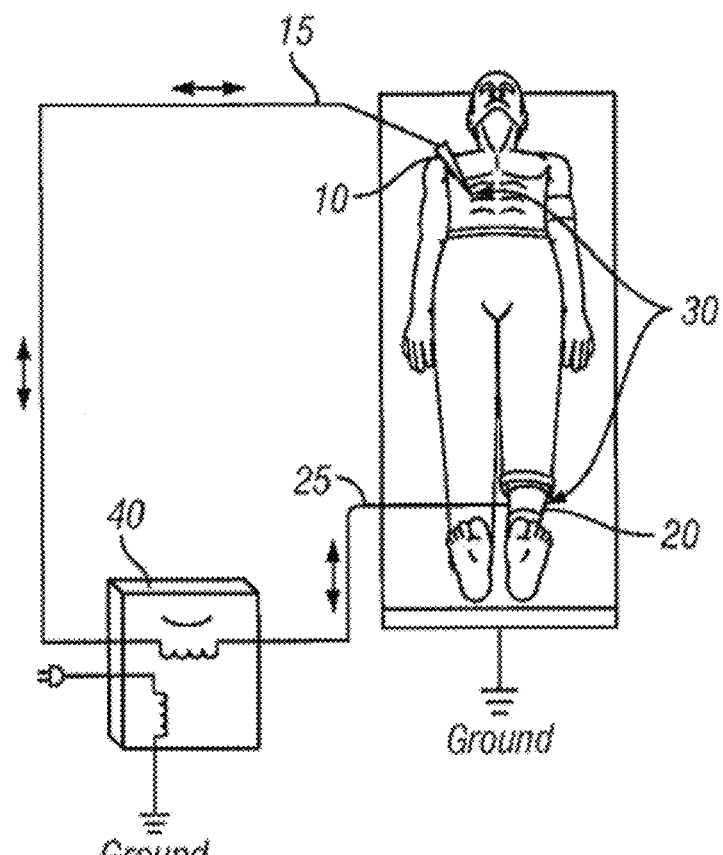
FIG. 1A is a drawing which illustrates the prior art traditional method of delivering monopolar high frequency electrical current to the human body during a treatment procedure.

In one embodiment, the present invention allows the general field of electrosurgery to use electrosurgical generators to power devices, such as instrument probes, developed for use in surgical and medical procedures.

More specifically, in one embodiment, the present invention relates to specific methods of connection of such devices to electrosurgical generators that provide active enhancement of output signal monitoring. Embodiments of the present invention also relate to specific management of circuit characterization when a single mode output from an electrosurgical generator is bridged to perform a circuit contraction in physical space.

The elements described herein relate generally to any electrosurgical generator that employs an active feedback monitoring algorithm designed to measure Voltage Standing Wave Ratio's (VSWR), total impedance change ($\Delta Z$), current fluctuation threshold/change ($\Delta I$), peak to peak voltage change or time-averaged voltage change ($\Delta V$) and other similar manipulations of the variables of Ohm's Law as it applies to radio-frequency transmission circuits into loads of time-varying overall impedance. Embodiments of the present invention are also useful to the general field of electrosurgery in which electrosurgical generators are used to power devices, such as instrument probes, developed for use in surgical procedures.

One or more embodiments of the present invention disclosed herein expands the functionality of the output ports of an electrosurgical generator through a bridging configuration that spatially contracts the heretofore separated independent poles of a monopolar system. Specifically, the bridging approach places the previously separated return (reference) electrode (commonly referred to as a return pad) in close proximity to the active (working) electrode through a reconfiguration of the connected device probe's circuitry. Additionally, passive and/or active electrical components are preferably employed in the completion of the bridge circuit to provide a rebalancing of the VSWR, $Z_{tot}$, $I_{max}$, $V_{pp}$ or similar control variable that is typically contained and monitored within the electrosurgical generator to provide safety feedback trip points for primary electrosurgical power output shutdown. This rebalancing is termed BALUN. As a result, the new bridge components are positioned in a way so as to act as bridge circuit maximum or minimum limits to activation based on the nominal variable of $Z_{tot}$ as measured between the output port of the electrosurgical generator and the active (working) end of the connected device probe. Furthermore, components used in the bridging circuit of the device may be selected to specifically mate with a specific type of electrosurgical generator and its corresponding control algorithm depending on the variable to which the specific generator is tuned.

The combination of the bridge circuit and passive/active components therein duplicating normal systemic control to the primary electrosurgical output power by modulating the reference signal to the electrosurgical generator monitoring circuit that enables early or delayed trip points dependent on the specific type and value of the components used in the bridging circuit. This added control creates the ability to connect lower energy devices to the electrosurgical generator that can be limited in their power capabilities below and within the spectrum of power output of the electrosurgical generator to which they are attached.

In some embodiments, the present invention can optionally be incorporated into an electrosurgical system that works in concert with specific instrumentation designed to take advantage of the bridge circuit configuration and reconfigured to work in a complementary manner from the electrosurgical generator output port to which it is attached. Simply put, this allows a) bipolar probe function from the monopolar output port of any given electrosurgical generator (termed the "primary" approach) and b) a reverse splitting of a bipolar output port into a monopolar output port or device is also enabled (termed the "reverse" approach). For the purposes of illustration, the primary approach will be discussed in more detail below with the understanding that the reverse approach will be subsequently obvious to those skilled in the art after studying this application.

With the primary approach the capability of monopolar output ports of electrosurgical generators is expanded and a new attached device functionality that has been designed in a bipolar configuration is provided. With the reverse approach, the capability of bipolar output ports of electrosurgical generators is expanded and a new attachment device functionality has been designed in a monopole configuration which is thus provided. With these advantages designed within the attached device to an electrosurgical generator, specific wave-form outputs, voltage, and current curves from the electrosurgical generator can now be applied in procedures from which they were previously excluded by definition, because of prior art's port-specific application. For example, in the reverse approach, existing monopolar devices are thus provided with the ability to use bipolar wave-forms at lower peak voltages and currents for procedures where tissue proximity requires greater care in managing the total current flow to prevent formation or delivery of excess localized energy.

Additionally, application of bridged signal circuitry to device instrumentation is not limited to "open" procedures, but can now also be applied to underwater environments that have previously been outside the application mode for some electrosurgical generators. Device configurations can now be specifically matched to procedures which are designed to utilize combined electrosurgical generator bridged output and instrument geometry. Both the low energy (tissue sparing) electrosurgical effects and higher energy (tissue ablation) effects can further be amplified through specific features or functions of the attached device and thereby improve the desired surgical outcome in relation to the amplified parameter.

Combinations of the above electrosurgical generator output ports and the use of a dynamically managed bridge circuit within the connected device become readily apparent for use within the gastro-intestinal system, urinary tract, thoracic cavity, cranial cavity, joints, wetted tissue, bone, and spinal column among others.

FIG. 1A illustrates the prior art's traditional method of delivering monopolar high frequency electrical current to the human body. The electrosurgical generator 40 is driven by AC-mains power and inductively coupled to the primary electrosurgical output power circuit 15. The primary electrosurgical output power circuit is electrically coupled to the monopolar hand piece device probe 10 and delivers electrosurgical current to the surgical site when manually directed by the hand of the surgeon on the device activation switch. The electrosurgical current then passes through the conductive media of the human tissues 30, whereupon it is typically routed by path of least resistance to the return electrode pad/plate 20 and returned to the electrosurgical generator return (reference) electrode via coupling cable 25. In this manner the electrosurgical current is passed from one pole (the active or working) to the second pole (the return or reference) at frequencies that range from 400 kHz to 1 GHz among others. Current passing through the human tissue zone 30 is not capable of being controlled to any extent by any portion of the electrosurgical system, except to start and stop the current flow itself. The dispersion and relative current density at any given point within the human tissues 30 is random and preferential to higher conductive tissues or electrical tissue reservoirs. As such, it is not uncommon for monopolar methods of electrosurgery to result in tissue burns within zone 30 resulting in tissue effects not associated with the intended surgical site. The invention disclosed herein overcomes the limitations of the fixed output port of an electrosurgical generator and the physical separation of the human tissue zone 30 required in the monopolar system by using balance/unbalance (BALUN) technology in the reference circuit bridge 25 to provide a new means of utilization for the monopolar electrosurgical generator in a bipolar fashion via the monopolar output port. This significantly decrease the risk of tissue burns or other unintended consequences of using monopolar system circuitry as established currently in prior art.

Figure 1B:
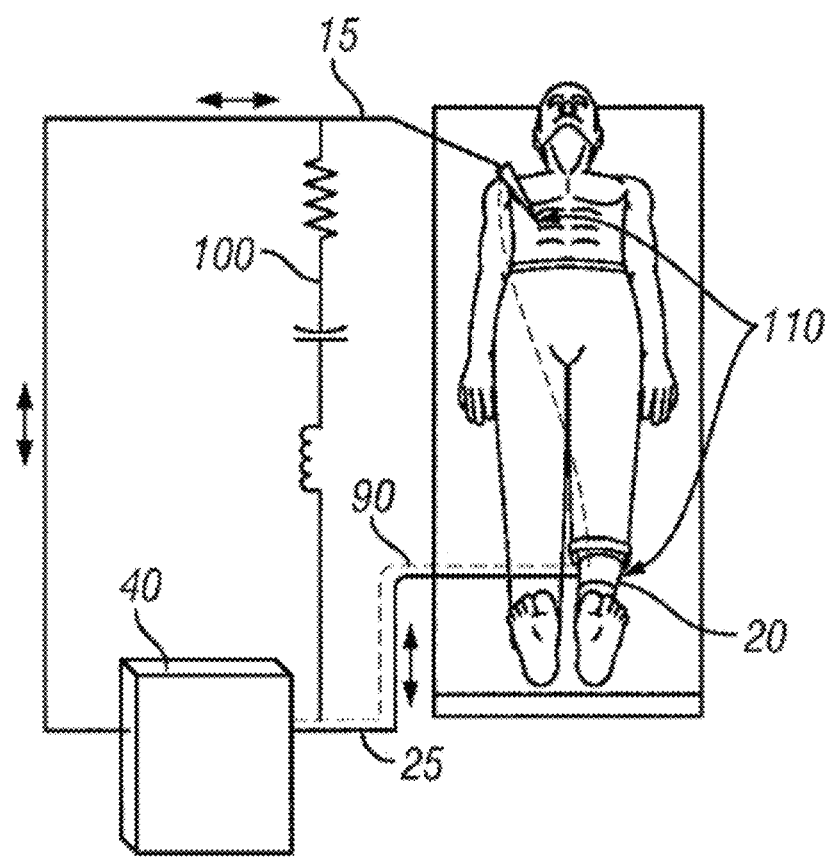
FIG. 1B is a drawing which illustrates the circuit bridge according to one embodiment of the present invention for use with a traditional electrosurgical generator whereby the bridge is within the device and its connector to the electrosurgical generator creating a bipolar circuit based device connected to the monopolar electrosurgical generator.

FIG. 1B illustrates the circuit bridge of the present invention for use with a traditional electrosurgical generator whereby the bridge enables the ability to use a bipolar device in a monopolar output port of an electrosurgical generator. As depicted, the general method by which the overall electrosurgical circuit is governed is shown. In simple terms, the electrosurgical generator circuit is nominally represented by a typical high-frequency transmission line. It therefore follows that such a high frequency transmission line can be modeled effectively through the use of the characteristic impedance equation:

$$Z_0 = \sqrt{\frac{R + j\omega L}{G + j\omega C}} ; \quad \text{(Eq. 1)}$$

where:
R=overall circuit transmission line resistance
G=overall circuit transmission line conductance
jω=the phase component of the circuit transmission line's active response elements
L=overall circuit transmission line inductance
C=overall circuit transmission line capacitance Since a typical electrosurgical generator transmission line consists of either closely spaced twisted-pair wires, straight-pair wires, or coaxial cable wires, the actual conductors of the overall circuit leads to a highly capacitive circuit orientation. Furthermore, the typical arrangement of the return electrode pad used universally in monopolar surgical configurations of the circuit forces an additional capacitive element if there is more than one electrical conductor used to provide the return pathway to the reference point. Dynamically, the variables with the greatest fluctuations intraoperatively when in use are a) the distance of the active (working) electrode to the surgical site, b) the conductivity of the interfacing media, c) the resistance of the active electrode (influenced by thermal properties; heat), and d) time-relative denaturation of tissue at the surgical site (related to conductivity of the interfacing media). Generally, the overall electrical parameters of those components of the system which are not immersed in the interfacing media at or near the surgical site tend to remain relatively constant by comparison. Thus, we can rewrite Eq. 1 in terms of those parameters that apply most prominently when operating the device to the characteristic impedance as:

$$Z_0 = \sqrt{\frac{(R_0 + R_D + R_t) + j\omega L}{\left(k \cdot \frac{A}{d}\right) + j\omega C}}, \quad \text{(Eq. 2a)}$$

Where:
$R_0$=material resistance of the circuit (resistance per unit length)
$R_D$=resistance (change) at a specific distance from the surgical site (monopolar only)
$R_t$=resistance change due to thermal heating of the active electrode
k=conductivity of the specific interfacing media
A=microscopic surface area (geometric area×roughness factor) of the active electrode
d=distance between the active and return electrode
Note that the $$\left(k \cdot \frac{A}{d}\right)$$

term is one typically applied for the determination of media conductivity in a conductivity cell. The treatment site when wetted with interfacing media of an electrolyte kind is very much the same type of environment. As such, the conductivity parameters apply with the distance d being on the order of 1-2 m. This simple fact, reveals how the connection between the active (working) and return (reference) electrodes is therefore governed mostly by the human tissues 30 (FIG. 1A) and not by the relatively small motions made by the surgeon during the act of treating the surgical site. The comparison is an order of magnitude in difference as the typical movement of the probe by the surgeon is on the order of 1 to 10 cm as opposed to the distance between the active (working) and return (reference) electrode in a traditional system as in FIG. 1A. Furthermore, the components $R_D$ and $$\left(k \cdot \frac{A}{d}\right)$$

effectively cancel each other out leaving the elements of the circuit that are most influential. A mark-up of the equation shows how these elements are cancelled:

$$Z_0 = \sqrt{\frac{(\cancel{R_0} + R_D + R_t) + j\omega \cancel{L}}{\left(k \cdot \cancel{\frac{A}{d}}\right) + j\omega C}} \quad \text{(Eq. 2b)}$$

This reveals that in the general case, the thermal-resistive and capacitive properties govern in the surgical environment.

FIG. 1B illustrates how the circuit bridging component can be bridged from the active RF output circuit to the primary return circuit in order to establish a "matched" impedance of the circuit to the load when the monopolar mode electrosurgical generator output port is bridged into the bipolar mode of the device, resulting in the elimination of the traditional return pad. This simple elimination requires that the external circuit within the device configuration be matched anew to the electrosurgical generator sensing pattern such that it will operate according to the standard output curves prescribed by the electrosurgical generator. By combining the appropriate and independent amounts of active circuit elements to the bridge, the matched impedance can be achieved for a bipolar device to function normally from the monopolar outputs of a traditional monopolar electrosurgical generator. This now provides a way to power bipolar devices with power curves that have been traditionally reserved for monopolar devices alone. Many of the typical power output curves used in traditional monopolar electrosurgery have characteristics that are known to be of advantage for certain applications and tissue types, but lack safety in the monopolar delivery method in many instances, such as with tissue sparing treatments. The same curves when delivered via a bipolar device can now do so with a highly improved degree of safety by avoiding current flow through random parts of the human body to connect with a distant return pad. There are several ways in which such a bridging circuit can be achieved to provide a matching mechanism to the circuit for mating with any one of a large variety of existing traditionally monopolar electrosurgical generators available in the surgical marketplace.

For example, in the treatment of articular cartilage, the goals of removing damaged portions of that cartilage are often complicated by excess tissue necrosis of surrounding healthy cartilage cells. This chondrocyte collateral damage is very notable with current devices of the prior art as the ability to control energy deposition with a monopolar device is limited. The return sequence of the traditional circuit obviates the ability to limit current deposition in the surrounding healthy areas. By the application of the bridge circuit and associated balance/unbalance technology disclosed herein, a bipolar device can be configured to be powered by a monopolar electrosurgical generator. This advantage eliminates the safety risk of prior art systems for energy deposition to collateral tissue and also eliminates the need for a bipolar electrosurgical generator as a power source. Further, the large spectrum of power settings and other configuration variables within a monopolar electrosurgical generator can be now applied to bipolar devices for further treatment flexibility that is enhanced with the fine tuning of energy delivery.

In FIG. 1B, bridge elements 100 can include any one or a combination of the types of components shown, which include but are not limited to capacitance (capacitors), inductance (inductors), resistance (resistors), signal amplification (op-amps), over-current protection (fuses, links, etc.), and other circuit components known to those skilled in the art. For existing electrosurgical generators that provide a circuit sensing function to determine overall impedance through active (working) electrodes and return (reference) sensing signals parallel to the active output line, bridge components may be added between the active output line 15, and the parallel sensing circuit and the return (reference) electrode line 25. This parallel sensing circuit is most often implemented as a "rider" signal on one of the primary power lines; either output or return (reference) and is denoted as element 90. This sensing circuit is typically filtered from the primary RF power signal and is used to determine the condition of the relative circuit impedance compared to the load impedance and is typically designed to "trip" when the two impedances become significantly imbalanced, indicating a fault condition in some part of the overall delivery circuit. In most cases such an imbalance is caused by a short or open circuit condition that evolves due to detachment of some element within the overall system such as, the return pad. Other fault conditions that can arise are averted by the present invention due to the elimination of the return pad and a provision of the electrical bridge that maintains the integrity of the sensing circuit and operability of built-in safety shut-down algorithm's within any ESU to which it is attached. The bridge circuit can be placed at any location between the output portal of the ESU and the electrosurgical hand piece distal tip.

As further depicted in FIG. 1B, the method of creating the bridging circuit allows for a single device 10 (as labeled in FIG. 1A), to now utilize the output of a monopolar port from an electrosurgical generator and bridge the distance 110, of the human tissues through which monopolar treatment current typically flows to the return pad. This joining of the active (working) 15 and return (reference) 25 electrodes in a single conductor has the benefit of expanding the use of the traditional electrosurgical generator consoles in ways that have been lacking until now. The pairing of the two primary conductors combined with the simultaneous elimination of the return pad is a net removal of active component influence from the overall electrosurgical generator system. The result is that in the bridging circuit, the same influence of active components must be restored in order to achieve a matched circuit into load condition.

As illustrated in FIG. 1B, the communication of the active components is not actually with the primary electrosurgical generator power output, but rather with a super-imposed "rider" signal that is typically used to monitor overall electrosurgical system conditions intra-operatively. This "rider" signal is typically conducted along the same conductors used for the primary electrosurgical power output but is graphically depicted as a separate conductor 90, for clarity of understanding in separating a super-imposed electrical high-frequency signal from the underlying power output signal. While the physical connection of active components 100, may be between the active (working) and return (reference) electrodes or pairs of either active (working) or return (reference) electrode leads, the values chosen for these components are not capable of exerting significant influence on the primary output waves of the high-power signal. The lower power "rider" wave however, is strongly influenced by these elements and as such is held in the matched state barring any significant changes at the working end of the bridged bipolar device 10. Additionally, within the same device, several electrode pairs can be designed whereby each electrode pair has its own bridge circuit characteristics so that the device can operate in a multimodal fashion. The multimodal fashion can be of any number of configurations, such as having the electrode pairs activated with their own switch on the device handle or that each electrode pair is activated differently based upon its position on the device.

Figure 2A:
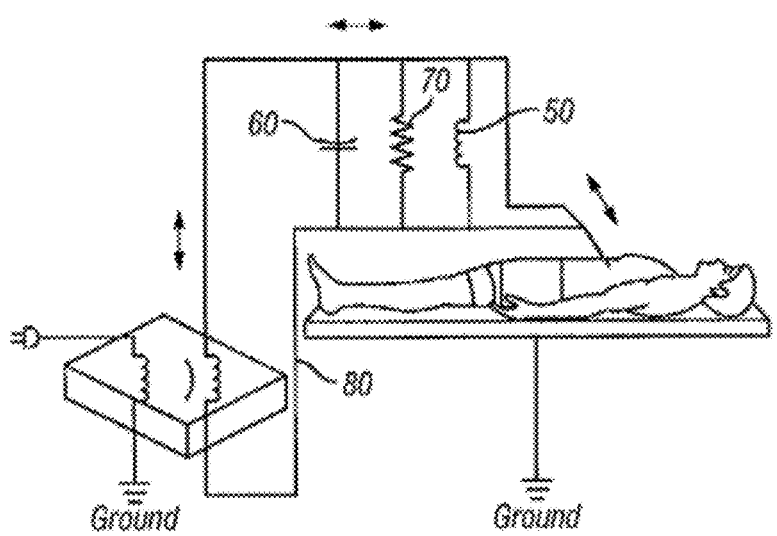
FIG. 2A is a drawing which illustrates an alternative placement of the preferred embodiment of active bridge components within the electrosurgical circuit outside of the electrosurgical generator.

FIG. 2A illustrates an alternative placement of the preferred embodiment of active bridge components within the device electrosurgical circuit. In this embodiment, the bridge circuit elements 50, 60, 70 are preferably arranged in a parallel manner to provide a greater influence to the return (reference) electrode for each element of the circuit. In this manner, the bridge circuit is created from parallel elements and is completed proximal of the hand piece 10 but distal to the electrosurgical generator. This embodiment illustrates how the traditional return pad is now eliminated while maintaining the matched condition of the overall circuit to the load encountered within the surgical site. It also demonstrates the multimodal configurations that can be incorporated into the device design based upon varying bridge circuitry per electrode pairs.

Figure 2B:
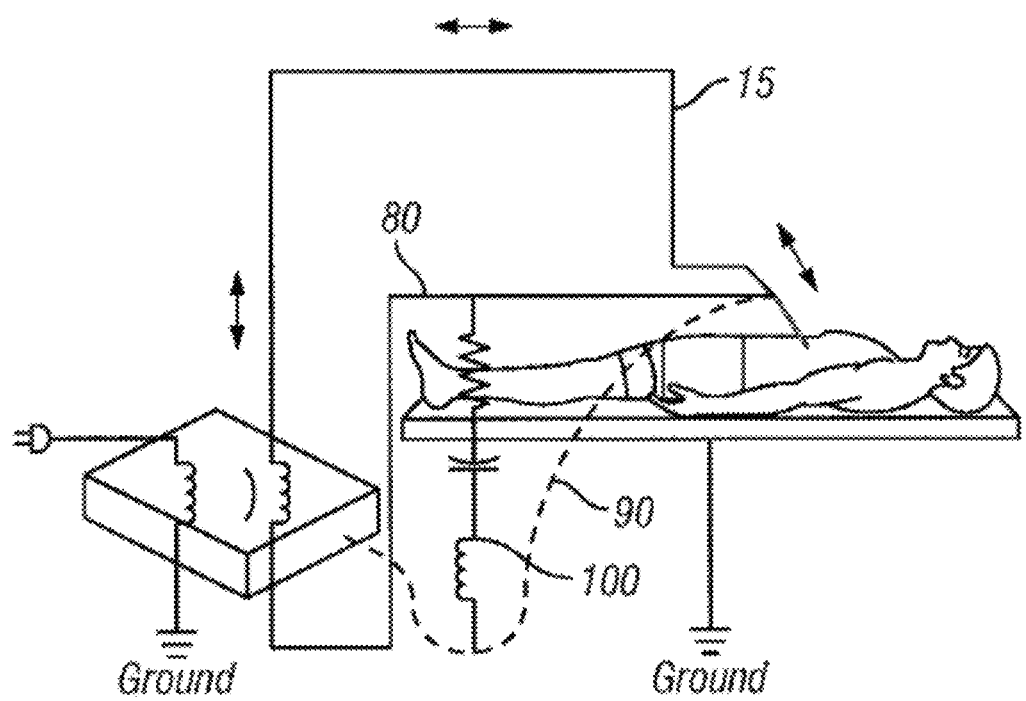
FIG. 2B is a drawing which illustrates an alternative embodiment depicting how the bridging circuit interacts with the return (reference) or sensing circuit.

FIG. 2B illustrates additional compositions and methods of use of an embodiment, wherein the interaction of the bridging circuit is directly with the theoretical sensing circuit line which provides for matching between the return (reference) line(s) to the electrosurgical generator output ports. The arrangement of bridge circuit 100 as shown can be in a parallel configuration, a series configuration, or any combinations thereof. While the physical connection of the components is preferably to the primary return (reference) or active (working) electrode lead lines, the effective communication of the bridging circuit is preferably with the "rider" frequency wave that is sent in a super-imposed manner along the same transmission lines, but measured via filtered sensing in an alternative test circuit to establish trip parameters for safe operation of the electrosurgical generator. FIG. 2B also demonstrates the multimodal configurations that can be incorporated into device design based upon varying bridge circuitry per electrode pairs.

Further detailed is the revised conductor set illustrating the joining of the monopolar active (working) and return (reference) electrodes and the complete elimination of the typical return pad 20 currently used in all monopolar procedures. The elimination of the human tissues bridge 30 (FIG. 1A) is also eliminated, thereby eliminating random energy propagations associated therewith. The super-imposed element of the "rider" frequency that is used to monitor overall electrosurgical circuit conditions intra-operatively is demonstrated. Active circuit elements 100 can be arranged in a multiplicity of methods such as but not limited to parallel, series, or blends thereof which yield preferential communication with the "rider" wave as opposed to the primary RF power wave due to specific values of the components designed for exactly that purpose.

Figure 3:
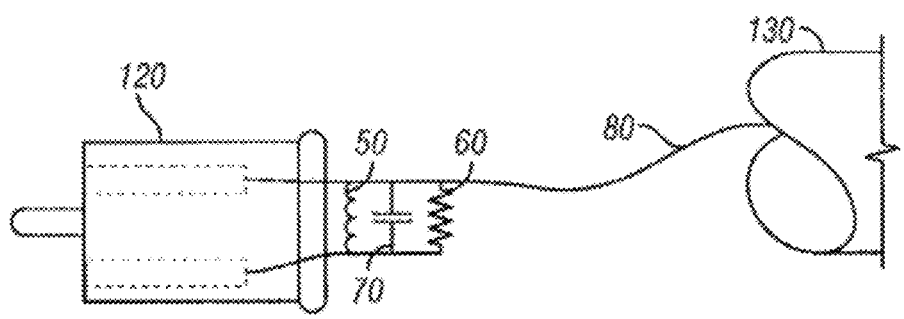
FIG. 3 is a drawing which illustrates a preferred embodiment for the bridge circuit in which the connector terminal of the active (working) or return (reference) lead-wire is bridged with the necessary components for circuit matching.

FIG. 3 is a detailed illustration of the preferred embodiment for the bridge circuit in which the connector terminal of the active (working) or return (reference) lead-wire is bridged with the necessary components for circuit matching. For universal dual wire connector terminals in traditional monopolar electrosurgical consoles, the dual wires are often used to conduct high-frequency "rider" signals that are measured or monitored in fault detection circuits for open, short, or high impedance conditions that signal undesirable surgical conditions. This signal is bridged with active components 50, 60, 70 to provide a matched circuit within a single jacketed conductor 130. Matching components can be placed at any point along the conducting pair to enhance or ameliorate the effects of linear resistance, capacitance, and/or inductance as the circuit may embody per unit length. Furthermore, such circuit components may be contained within the connector terminal itself to provide for both protection and structure for retention of such components.

Figure 4:
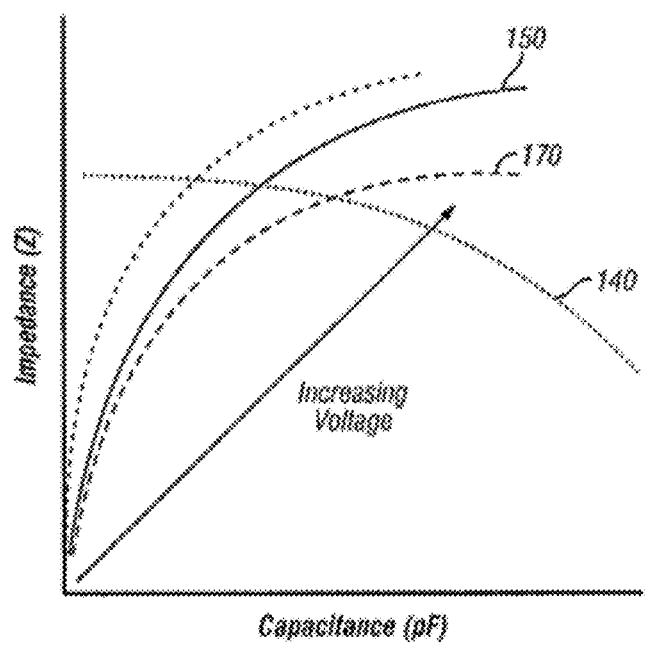
FIG. 4 is a graphical representation of the characteristic impedance threshold limits and operational envelope of the preferred embodiment within existing safety envelopes of typical electrosurgical generators.

FIG. 4 is a graphical representation of the characteristic impedance threshold limits and operational envelope of the preferred embodiment within existing safety envelopes of typical electrosurgical generators. With respect to increasing capacitance up to or beyond the matched load condition of curve 150, there is no change in the point at which the electrosurgical generator sensing circuit will detect that the characteristic impedance of the overall output circuit has been exceeded. Threshold 140 is typically governed by a non-linear software algorithm that seeks to maintain a maximum voltage output, maximum current flow, at a minimum deviation from a user-selectable output value. Conditions where excessive capacitance is introduced into the circuit yields imbalanced curve 170 that will decrease the overall circuit characteristic impedance (ref. Eq. 2b) beyond the limit for any given user-selection of output. Similarly, in the theoretical case of complete elimination of all capacitance from the circuit, the overall characteristic impedance would approach zero. This is purely a theoretical condition as the existence of paired wires introduces a minimal amount of capacitance/resistance (impedance) that prevents the absolute zero condition from ever emerging. External modifications of parameters contained within Equation 2b, inevitably result in arrival at threshold points sooner than the matched condition and the matched condition represents the ideal arrival point at safety thresholds that do not modify electrosurgical generator output performance.

The bridging circuit operation is designed to provide an impedance matching equivalent circuit as seen by the output ports of a traditionally monopolar electrosurgical generator. Since no internal components of the electrosurgical generator are affected by this invention, the matching that the bridge circuit provides has no effect on the normal safety parameters of the electrosurgical generator and by definition forces the attached device containing the bridge circuit to operate within the safety envelope of the electrosurgical generator to which it is attached. This is clearly illustrated mathematically when the reduced version of equation 2b, shown as equation 3, is reviewed as shown below:

$$Z_0 = \sqrt{\frac{(R_0 + R_i) + c}{j\omega C}},$$ (Eq. 3)

where c=a constant inductance.

As described in FIG. 4, the alterations of elements of this equation that alter the circuit characteristic impedance result in an imbalanced condition of the circuit that by definition creates conditions in which safety circuit shut-down of the attached device will occur at premature points relative to the optimal output of the electrosurgical generator. This has a dual advantage in that safety is maintained in unbalanced conditions, and simultaneously that the matched circuit state provides a peak output that is no greater than the electrosurgical generator is capable of under its ideal conditions at the output port as manufactured.

Accordingly, the use of a bridging circuit opens up new and more expansive uses for the power-outputs and associated wave-forms of those power outputs from monopolar electrosurgical generators that can now be employed in a bipolar manner, thus enabling broader treatment options for the wide variety of human tissues encountered in most surgical specialties. The bridge circuit for joining of monopolar outputs into a single bipolar device may be completed via multiple means, which include but are not limited to connector terminal bridging, conductor cable bridging with flexible circuit components, and bipolar handpiece bridging with a variety of PCBA approaches.

Figure 5:
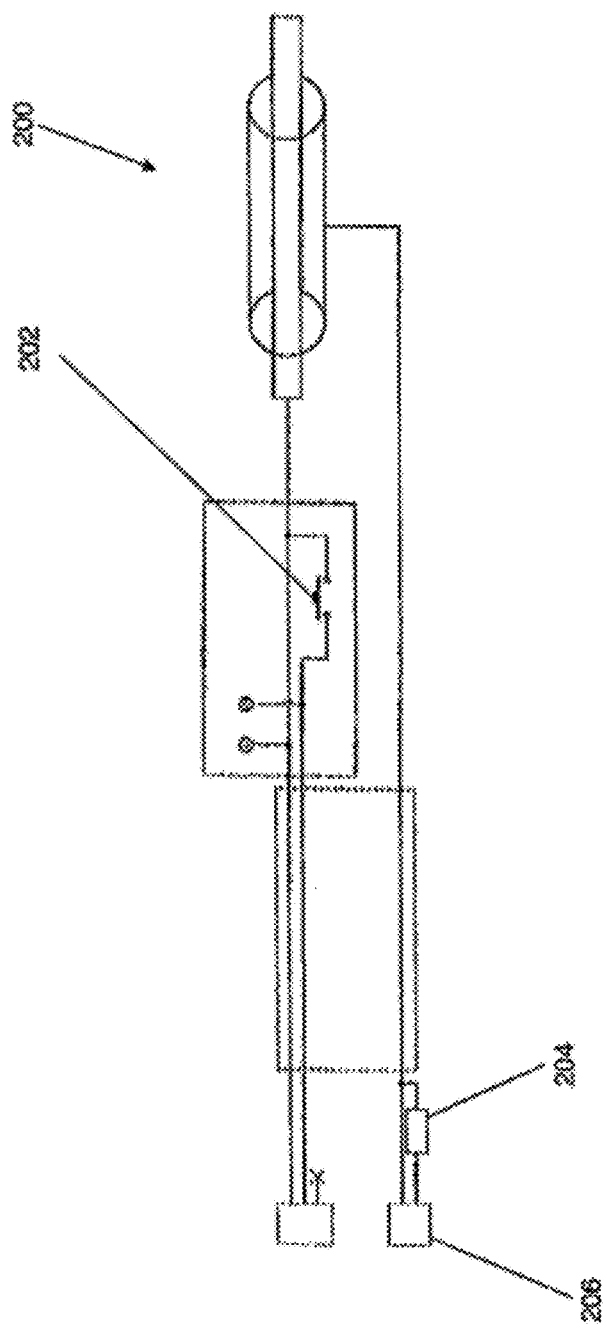
FIG. 5 is a drawing which schematically illustrates an embodiment of the present invention wherein a single active electrode is connected to a single switch.

FIG. 5 schematically illustrates an embodiment of the present invention wherein a conducting portion of bipolar electrosurgical probe 200 is electrically connected to switch 202 and wherein another conducting portion of bipolar electrosurgical probe 200 is electrically connected to component 204. In this embodiment, component 204 most preferably bridges a plurality of connectors of the return cable connector through 206. Component 206 is most preferably selected to have a value such that a monopolar electrosurgical generator unit detects an impedance, when used with bipolar electrosurgical unit 200, which impedance is substantially similar to that encountered when a monopolar electrosurgical probe is used with the generator. Accordingly, those skilled in the art, upon studying this application, will readily appreciate that component 206 can comprise an inductive value, a capacitive value, a resistive value, and/or combinations thereof, depending upon the generator to which bipolar electrosurgical probe 200 is connected. Optionally, component 206 can be a variably-adjustable component or plurality of variably-adjustable components such that a user can adjust the one or more components 206 to create an overall probe impedance which is substantially similar to that of a monopolar probe connected to the generator.

Figure 6:
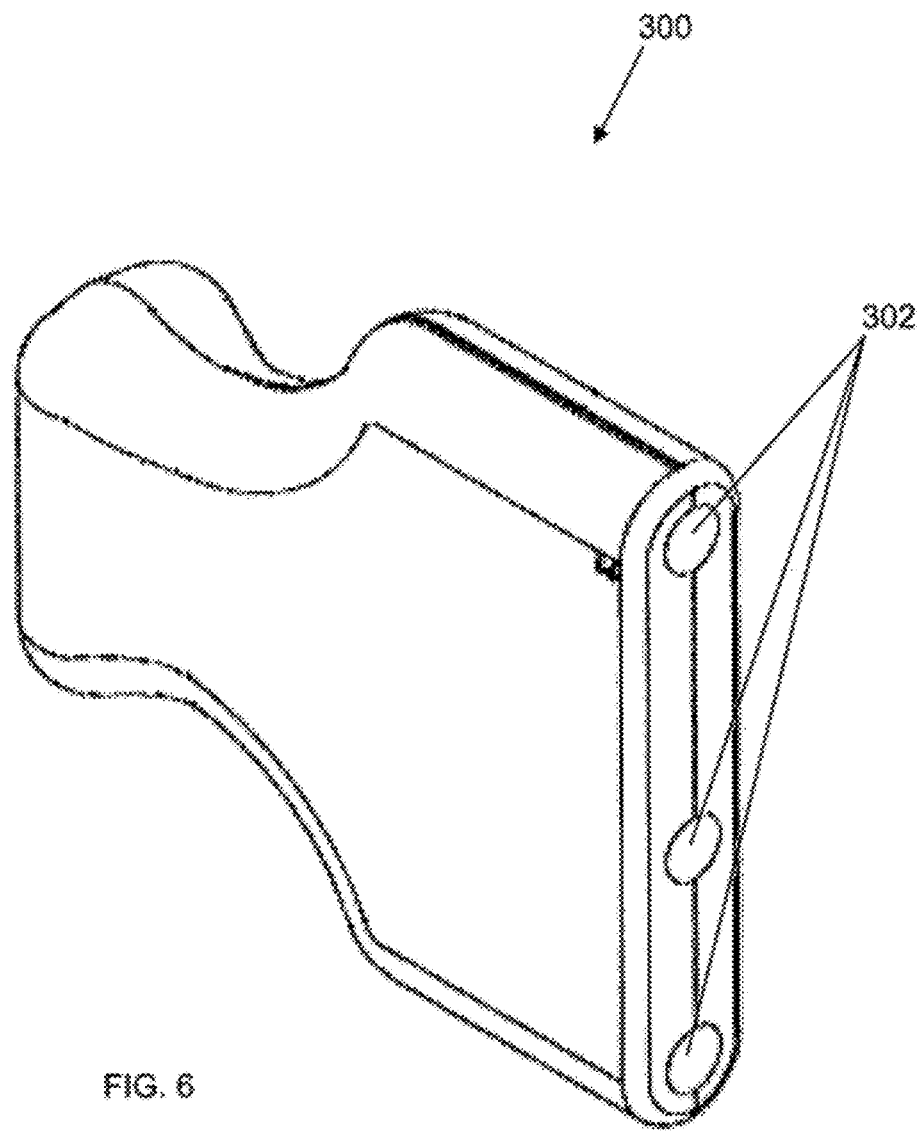
FIG. 6 is a drawing illustrating a universal connector as can be modified in accordance with the teachings of one embodiment of the present invention.

Traditional electrosurgical mono-polar devices use what is termed in the industry as a "Universal Connector" 300, which is configured with 3-pole contacts 302 as illustrated in FIG. 6. The purpose of these connector poles is to provide dual functionality of cutting and coagulation at the distal tip of the working device. By design, wiring connected to each of the poles in the connector are routed to a collocation point where the individual wires are then bundled together through an insulating/protective jacket where they are further routed to the hand piece along a roughly 3-meter length of cabling. The circumstantial configuration of the cabling leads to several electrodynamic functions that must be compensated for when using a bridging-circuit approach in the conversion of a traditional mono-polar circuit to a bi-polar circuit. Of primary importance is that the bridging circuit contains the anticipated magnitude of impedance and that such impedance has the correct characteristic/type of impedance; meaning capacitive, inductive, and resistive or a combination thereof.

In one embodiment, the present invention comprises a conventionally-shaped universal connector which comprises only two of the typical three conductors. Accordingly, in one embodiment, the present invention comprises a conventionally-shaped universal connector which has only two conductors disposed therein and, of which, one conductor(s) are for the common (reference) conductor and the remaining conductor used is placed in either the coagulation conductor location or in the cutting conductor location. In an alternative embodiment, a conventional universal connector is provided with all three of the conductors, however, only two of the three conductors are electrically connected to the cabling leading to the hand piece.

As previously discussed, in an embodiment of the present invention, there is preferably the elimination of conductor comparably from that of a standard three conductor universal conductor 300 as the underlying functional power delivered to the hand piece from a single port of the electrosurgical unit is enabled to perform with improved control for use in both surgical functions of cutting and coagulation, thus providing surgical effect at lower energy output levels than heretofore contemplated by industry. Elimination of one of the conductors is useful since there exists, within the electrosurgical generator, reference ground planes that induce capacitive-coupling in wiring that contains the third functional pole and corresponding wire. These effects are known to those skilled in the art, and are typically referred to as "cross-talk" where unshielded wiring is routed in close proximity. The phenomenon is a function of the propagated electro-magnetic wave that is inadvertently "tuned" to an antenna of approximately 3-4 meters. Thus, a cable of the same length acts as an ideal "antenna" and receives these signals that subsequently generate spurious currents on the third pole and its corresponding wire. Spurious currents can have several detrimental effects when uncontrolled or ignored within the system of operation. In the case of the prior art, there exists the chance of control function triggering signals being overridden by antenna effect currents. Additionally, there exists a reverse condition, wherein the electrosurgical generator port that is not intended for use can, through capacitive coupling, conduct its output energy in a variable manner to the working end of the hand piece. This can result in a cutting level of energy output reaching the working end of a device when it is unintended. An improved method of achieving the desired output at the distal tip of the device is to remove the secondary higher energy conductor (i.e. the cutting conductor) thereby ensuring that no spurious currents are induced in an uncontrolled manner to the distal end of the device or to the electrosurgical generator that could destabilize operation.

In one embodiment, the present invention preferably uses only two of the typical three outputs of universal connector 300. Accordingly, in one embodiment, the present invention uses only the common conductor and either the cutting output conductor or the coagulation output from a monopolar electrosurgical generator. Embodiments of the present invention eliminate the need for a dual function control mechanism through the advancement in understanding of distal tip electrode geometry and surface area relationships between the active and return electrode. This improvement provides for sufficient energy concentrations at the active electrode to be built up such that performing surgery across a broader range of power effect levels/functions is possible without the need of a different power output portal. Thus, the bridging circuit of the present invention also requires the elimination of at least one of the primary power output conductors of the universal connector to provide the preferred embodiment of lower energy level operations whilst simultaneously producing equivalent surgical effects to those devices of the prior art. It is through the use of and amplification of surgical effect in the lower energy bands of RF electrosurgical power output that tissue is thereby preserved and protected from exposure to excessive current or heat. The resulting surgical effect is the ability to perform traditional underwater surgery at power levels previously thought insufficient to perform surgical procedures from the coagulate only mode.

Given the above teaching, it should become clear to one of ordinary skill in the art that this method of use can be applied to the various modes of output from traditional electrosurgical generators resulting in yet further expansion of availability of power-output levels and wave-forms that have been limited to single mode operation heretofore. This expanded availability provides for greater functionality of the devices attached to sophisticated traditionally monopolar electrosurgical generators through broader arrays of energy availability to bipolar device modes that yield more controlled outcomes and greater predictability of those outcomes for most tissue types encountered in the surgical specialties.

The reverse approach as described above can similarly be designed for use in electrosurgical generators that use a bipolar output port that is to enable use of monopolar and bipolar devices to effect tissue treatment. The use of embodiments of the present invention as described herein provides the additional benefits of eliminating excessive equipment in the surgical suite and a reduction in required equipment space without significant added cost to the operative outcome of the electrosurgical approach. In addition, new high peak-to-peak voltage wave-forms, heretofore used only in monopolar methods, are thus also provided for bipolar systems. In addition, mixed-mode cutting and coagulating wave-forms previously relegated to monopolar systems are now also provided for bipolar systems in accordance with embodiments of the present invention.

In an embodiment of the present invention, as illustrated in FIGS. 7 and 8, a plurality of active electrodes can optionally be provided which electrodes can optionally be connected to a single switch or to a plurality of switches such that each active electrode can be simultaneously or selectively activated.

Figure 9A:
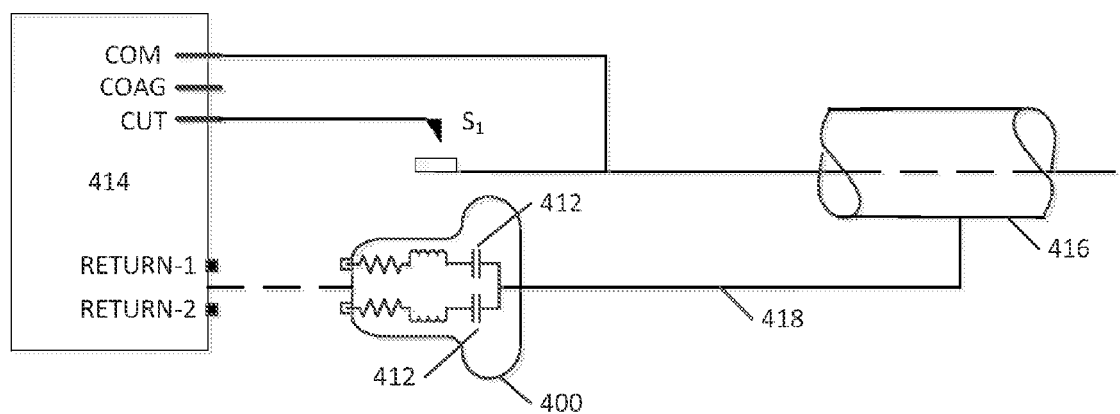
FIGS. 9A and B are drawings which schematically illustrate embodiments of the present invention wherein parallel-arranged components are disposed within a connector that connects a hand piece to an electrosurgical generator.
Figure 9B:
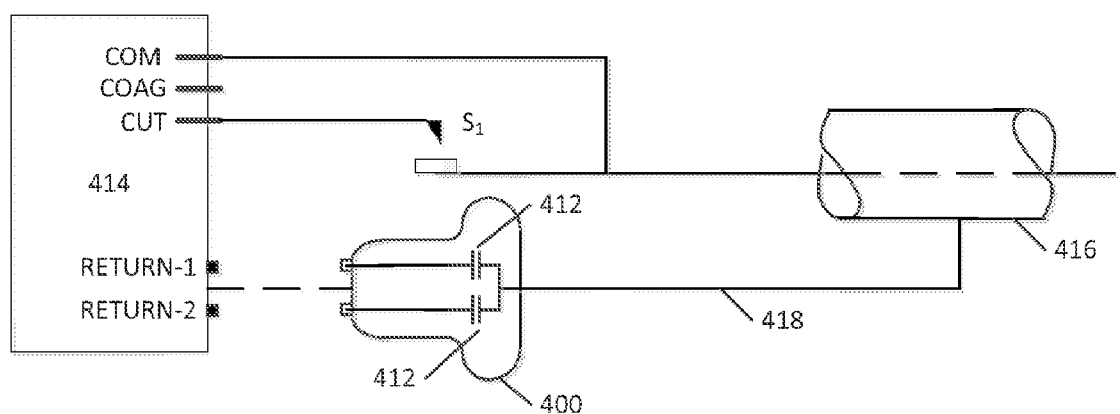

As best illustrated in FIGS. 9A and B, an embodiment of the present invention relates to specialty connector 400 which houses an electrical component 412, that provides correct sensing circuitry feedback to electrosurgical unit (ESU) (also herein referred to as a "generator") 414. In one embodiment, one or more components 412 can be provided. In one embodiment, wherein a plurality of components 412 are provided, they are preferably tuned to match an output signal and nominal impedance signature of a return electrode sensing circuit of ESU 414. As each manufacturer of the various ESU consoles may use a custom algorithm and/or electrical circuit for detection of the return electrode pad in monopolar applications, the potential for electrosurgical probes 416 needing ESU-specific impedance signatures has always existed. Optionally, various types and/or values of components 412 can be used in order to provide an expected return signal for different generators 414. For example, as best illustrated in FIG. 9A, electrical components can be an arrangement of various types of active and passive components, such as inductor, resistor, and capacitor in series with one another, which is placed into a parallel configuration with another inductor, resistor, and capacitor, as is illustrated. Optionally, however, components 412 can comprise a single pair of active or passive components. For example, components 412 can comprise a pair of capacitors as is illustrated in FIG. 9B. Of course a combination of two or more capacitors arranged in series and/or parallel can be used to form one or more of active components 412, such that a most preferred total capacitance is obtained. While embodiments of the present invention provide desirable results when all or some of electrical components 412 are disposed within the confines of connector 400, alternative embodiments wherein all or some of the electrical components are not disposed within the confines of connector 400 can also produce desirable results. For example, in one embodiment, component 412 can be formed into another housing, which can optionally include a housing formed within cable 418. Alternatively, for embodiments wherein a pair of capacitors is preferably used, such capacitors can optionally be formed from one or more portions of cable 418. For example, cable 418 can comprise a first conductor leading from return 1 of ESU 414 which is positioned in close proximity to a second conductor leading from return 2 of ESU 414 and which conductors are separated by a dielectric, thus forming a predetermined capacitance. Likewise, in a similar fashion inductors can also be formed from coiled portions of cable 418 and resistive values can also be provided from cable 418 being constructed with a material which provides a desired resistance over a predetermined length of cable 418. The broken line between 400 and return 1 and return 2 illustrates the engagement of the tips of 400 with return 1 and return 2.

Figure 19:
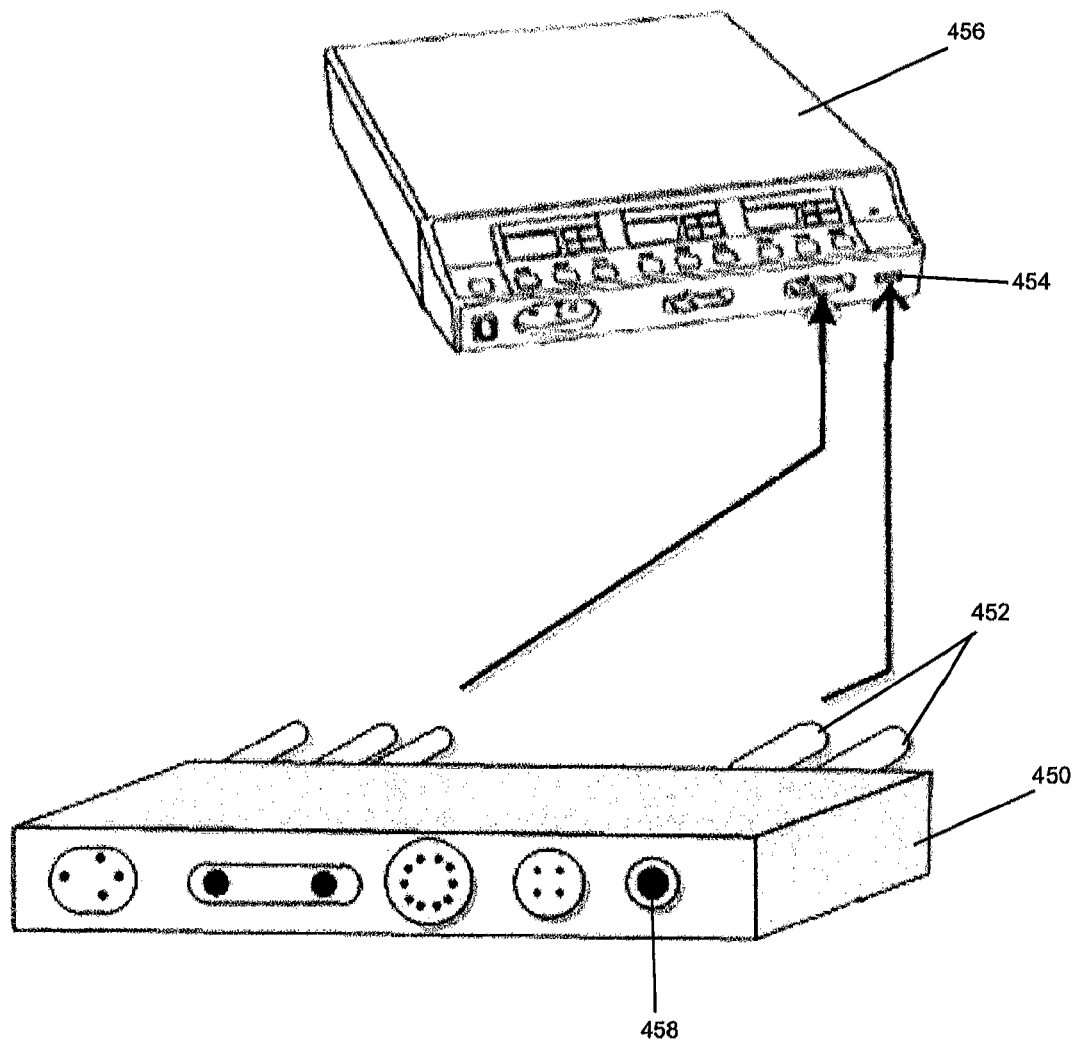
FIG. 19 illustrates an embodiment of the present invention wherein an adaptor is connectable to an ESU such that a bipolar hand piece can be powered by a monopolar output of the ESU.

Referring now to FIG. 19, in one embodiment, the present invention can include adaptor 450 which can include one or more generator connection points 452 which are preferably positioned to make electrical connection to one or more monopolar connection points 454 of ESU 456. Adaptor 450 preferably comprises one or more bipolar hand piece connection points 458. In one embodiment, hand piece connection points 458 can comprise connection points for a single type and/or make and model of a hand piece, or connection points 458 can comprise connection points that permit numerous types and/or makes and models of hand pieces to be connected into ESU 456. Adaptor 450 preferably comprises internal connections and one or more active components as previously taught which permit a bipolar hand piece to be powered from a monopolar output of an ESU. For example one or more active components can preferably be provided such that the patient return connection point(s) of the ESU see an expected return signal from a monopolar hand piece when a bipolar hand piece is actually what is being powered by the ESU.

In one embodiment, the one or more active components can be disposed anywhere along the circuit path which travels from the generator to the hand piece and back to the generator and such components thus need not necessarily be disposed in a connection mechanism of the hand piece. For example, in one embodiment, such components can optionally be disposed within the hand held portion of the hand piece itself.

INDUSTRIAL APPLICABILITY

The invention is further illustrated by the following non-limiting examples.

Example 1

Figure 10:
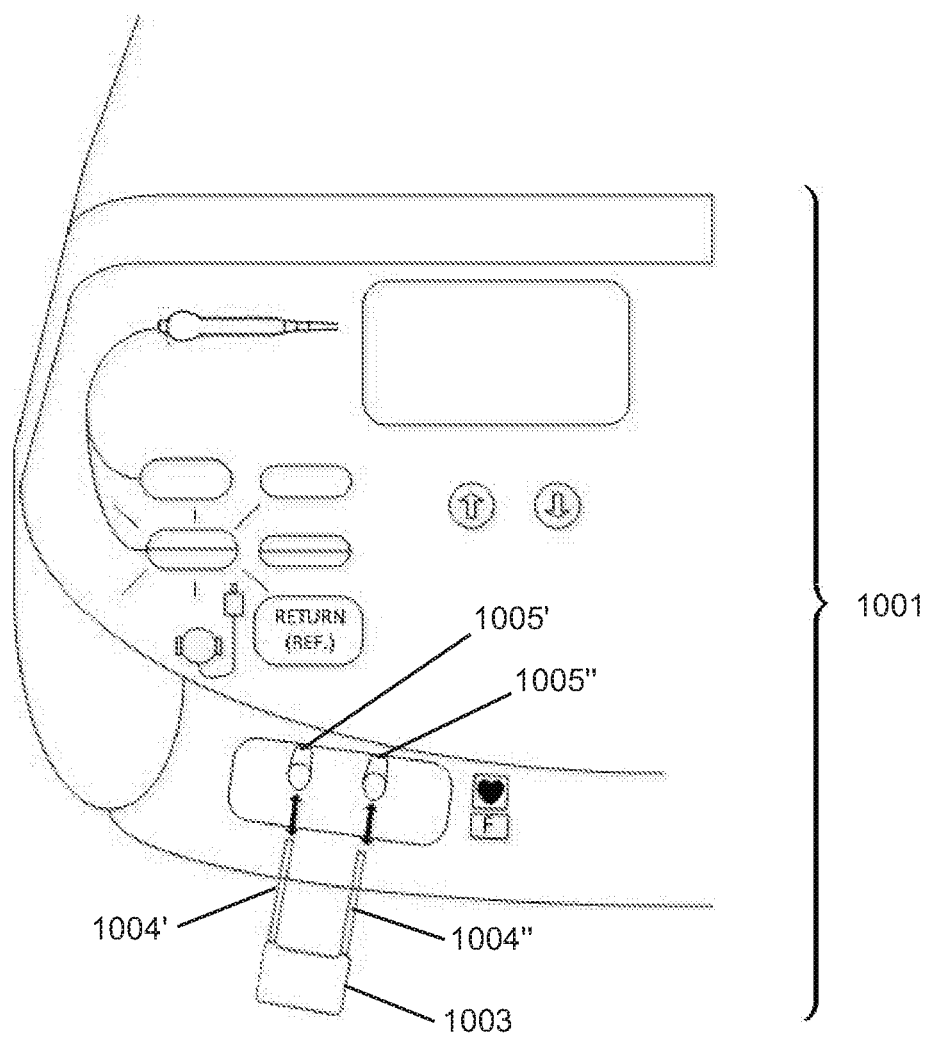
FIG. 10 illustrates an experiment that was performed wherein a capacitor is shorted across the electrode terminals of electrosurgical unit ("ESU")

A CONMED®, System-5000, Electrosurgical Generator, Mod. No: 60-8005-01, SN: 03DGP287, Calibration Date: Unknown, as well as three CERULEAU®, ES-300-35, RF-Probes, Lot. No: 02101000014, where obtained and modified as indicated below for ESU impedance signature matching. Capacitors of varying values and types (polymer, ceramic, electrolytic) as identified below were used to isolate the capacitive magnitude required for ESU impedance signature matching. Saline solution 0.9% by weight was used to test nominal ESU console output into load (~120 w) and stability of return electrode pathway circuit. The basic method for capacitive evaluation was initiated by using capacitors of various values and types in a "short" condition across ESU return electrode terminals as illustrated in FIG. 10. Referring now to FIG. 10, capacitor 1003 having connector 1004' engages with return electrode terminal 1 1005' and connector 1004" engages with return electrode terminal 2 1005" of ESU 1001.

The general band was identified and then subsequently bisected to arrive at a nominal "center" point for capacitance signature of the circuit. Once the correct center point was properly identified, small scale form-factor components were procured from electronic component supply houses to further evaluate heating effects, robustness, and appropriateness for use in normal construction.

Factual information regarding the ESU is illustrated in the table of FIG. 11. Various capacitors were employed to find the location in the capacitive domain for which the ESU would recognize an impedance signature as equivalent to that of a nominal return pad. The table of FIG. 12 below illustrates the basic findings that identified the general "band" in which capacitive impedance is an acceptable signature for that ESU.

Initially, it appeared that there was an impedance step-change in the general signal response/measurement of the capacitive signature on the return pad circuit. As the driving signal voltage, current and frequency was unknown, the exact impedance value at which the impedance step-change took place was an unknown. Regardless of the exact parameters, it was clear that a capacitive circuit signature below about 0.05 μF has impedance that is out of range for the return pad sensing algorithm of the particular make and model of ESU.

Within the band of about 0.05 μF to about 100 μF, there is a band of recognition that appeared to be within the correct impedance domain. However, as that ESU was capable of determining what type of return pad (split or single) was being used, the console indicated a rough division between the two types of pads around 0.37 μF. "Single" type return pads are legacy systems in electrosurgery and are encountered less frequently, as they do not provide ideal patient protection against skin burns in monopolar surgical applications. While it is logical that recognition of legacy (single) type return pads be enabled on a general surgery ESU, in relation to embodiments of the bipolar probe connection of the present invention, either type of recognition is likely satisfactory. Manufacturer's publications regarding the internal circuitry and algorithms of the ESU were not available to the inventors. It is highly unlikely, given the historical evolution of legacy systems in electrosurgery, that a minor type difference in the return electrode pad should cause the ESU to produce a different output signal.

It is helpful to recall how capacitance is calculated and understand its net response/impedance within an alternating current ("AC") circuit. This permits a better grasp of the situation with respect to the return pad sensing circuit as it is implemented on the ESU. The formulae were used to create test values of capacitance (using series and parallel combinations) across the return electrode terminals while observing console response. The equations below calculate ideal capacitance for multiple capacitors in series and in parallel. FIG. 13A illustrates a simple circuit and basic equations for calculation of current and alternating current voltage drop across a capacitor. FIG. 13B illustrates a simple circuit and a basic equation for calculation of impedance (Xc) produced by a capacitor.

Series Capacitances $$C_{total} = \frac{1}{\frac{1}{C_1} + \frac{1}{C_2} + \ldots \frac{1}{C_n}}$$

And;

Parallel Capacitances $$C_{total} = C_1 + C_2 + \ldots C_n$$

Note, that for capacitors in series, the total capacitance will always be smaller than any of the single capacitor value(s). Conversely, parallel capacitances are simply added to arrive at overall values. In this way combinations of series/parallel conditions were used to approximate exact values within the spectrum for which operation was anticipated.

In order to properly select the capacitor values for use with the ESU, it was necessary to keep in mind the following overall constraints which the new capacitors preferably met in order to avoid disruption to either current manufacturing process, tooling or both:

Capacitor form-factor was preferably less than 4.5 mm dia.×5.5 mm length;

Capacitor form-factor was preferably axial;

Capacitor tolerance rating was preferably ±20% or better (smaller);

Capacitor voltage raging was preferably 50 Vdc or better (higher);

Capacitor was preferably able to withstand worst-case activation during (30 min continuous) without dielectric breakdown or overheating (45° C. max); and Capacitors were preferably readily available from more than a single source supplier.

FIG. 14 is a table which illustrates that a rough ideal center-point for capacitance appeared to occur at about 0.15 µF with approximately a 0.7 µF tolerance on either side of that center that remained within the "split" pad recognition zone with high degrees (more recognition display bars) of confidence.

Commercial Availability and Tolerance Studies: For any value of capacitor that was selected, the inventor took the into consideration the normal variation of capacitor manufacturing that is called out in specifications for such components. Typically, commercially available capacitors were available in two grades of capacitance tolerance ±10% or ±20%, with the obvious concomitant cost implications of more accurate tolerance.

Based on the initial results of the table of FIG. 14, a mathematical calculation of series resistances was made to determine ideal capacitor values for the CERULEAU® probes connecting to the CONMED® ESU. Series wiring across the terminals was ideal, providing a parallel inter-capacitor connection to the probe's return electrode conductor, thus allowing for balanced current flow return to the ESU.

FIG. 15 illustrates how the capacitor orientation was made for current ESU connections, similarly providing balanced current flow. Capacitor 1503 connects line 1506 to connector 1501 wherein 1501 engages with return electrode terminal 2 and the line engaged with return electrode terminal 2 is shown at 1506. Capacitor 1504 connects line 1505 to connector 1502 wherein 1502 engages with return electrode terminal 1 and the line engaged with return electrode terminal 1 is shown at 1505. FIG. 15 is a detailed view of electrical connector 400 of FIG. 9B. Line 1505 and 1506 connect with line 418 of FIG. 9B.

Noting that it is most advantageous in the manufacturing environment to provide for capacitors of identical values to avoid production line controls/confusion should different values be required for the two components, we applied the series calculation for capacitance from above:

Series Capacitance Quick Calc:

$$C_1 := .3 \, \mu F$$

$$C_2 := .3 \, \mu F$$

$$C_{2series} := \frac{1}{\left(\frac{1}{C_1} + \frac{1}{C_2}\right)} \quad C_{2paratot} := C_1 + C_2$$

$$C_{2series} = 0.15 \cdot \mu F \quad C_{2paratot} = 0.6 \cdot \mu F$$

Thus, in the embodiment illustrated in this experiment, the theoretical ideal capacitance for the center was found to be two 0.3 µF capacitors connected in series across the terminals with inter-capacitor connection of the return electrode wire. However, upon investigation into commercial availability, it quickly became apparent that this value for commercial components was virtually non-existent. The two nearest readily available values that met the basic requirements from above were: 0.22 µF and 0.33 µF.

Those values of components in series produce the following overall ideal capacitance:

$$C_1 := .22 \mu F$$

$$C_2 := .22 \mu F$$

$$C_{2series} := \frac{1}{\left(\frac{1}{C_1} + \frac{1}{C_2}\right)} \quad C_{2series} = 0.11 \cdot \mu F$$

$$C_1 := .33 \mu F$$

$$C_2 := .33 \mu F$$

$$C_{2series} := \frac{1}{\left(\frac{1}{C_1} + \frac{1}{C_2}\right)} \quad C_{2series} = 0.165 \mu F$$

From the calculations, it was clear that either value would be nominally capable of meeting the approximate required capacitance; with the 0.33 µF capacitor being the more favorable.

The table of FIG. 16 charts the two capacitor's published specifications vs. the minimum requirements Data available from an on-line electronic components supplier suggested that there were multiple options nearly ideal for the application in question. Thus, toward the end of understanding base functionality, larger scale components of the same values were sought from local suppliers to test as prototypes. The goal was to verify that the calculated values would produce a workable product using the identified assembly approach. Of the two capacitor values, only the 0.22 µF were available from the local supplier, but they were available in two material configurations; polymer and metalized film. Both were procured to verify that materials of construction would have no significant effect on performance.

FIG. 15 illustrates the configuration that was prototyped to evaluate 0.22 µF connection while applying the full output range capability from the ESU.

The ESU accepted the probe with the installed capacitors with a fairly high degree of "lock", as was represented by the number of bars illuminated out of the total bars of "lock" that were available.

There was a partial (6 out of 8 bars) lock at first connection of the probe using the inter capacitor connection on the 0.22 µF caps.

Upon first firing at the lowest output level of COAG power (Fluids mode; pinpoint signal), the lock signal was boosted automatically to register a complete (8 out of 8 bars) lock immediately after the first firing of RF-power.

From the response of the generator, it appears that the electrical sensing circuit was looking for a minimum initial "lock" and once the primary RE power loop was closed for the first time, the "lock" signal was boosted automatically to full status for the remaining operation of the "mains on-cycle" of the ESU console with that specific probe.

During the "mains on-cycle" of the ESU depicted above, the power level was worked through all modes (General, Fluids, Lap) and all COAG power output signals (Spray, Spray-Pulse, Standard, Standard-Pulse, and Pinpoint) up to the maximum rated wattage output for each mode/signal combination. In no instances did the ESU exhibit any intermittent or abnormal behavior. No errors were observed and no audible alarms were witnessed.

Commercial availability of capacitors was then explored in greater detail, given that a macro-scale, prototype proved viable. Basic availability and cost factors (Ref. Att.-2) were already investigated and detailed sizing was investigated to determine overall applicability of proposed form-factors.

Figure 17:
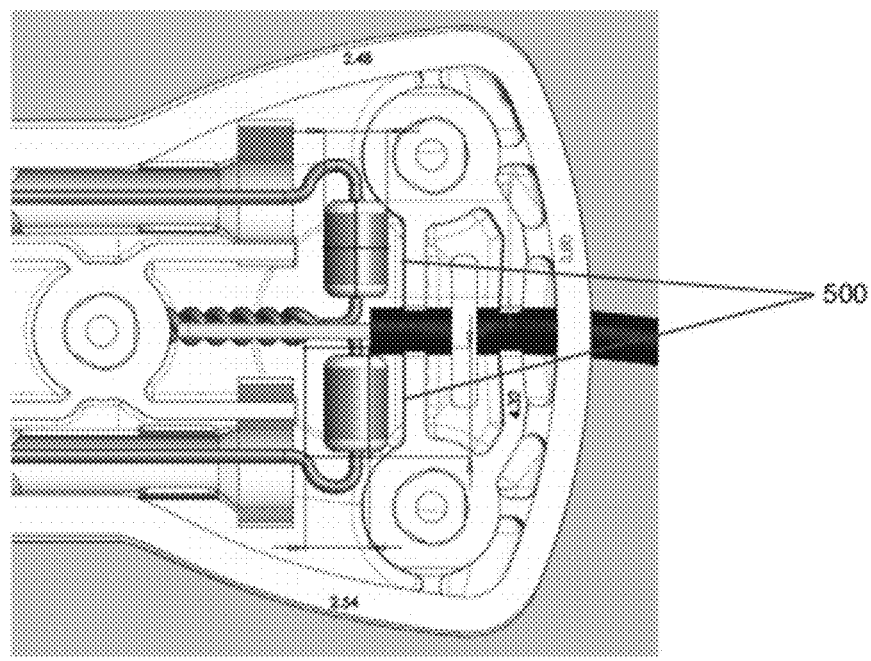
FIG. 17 is a drawing which illustrates an embodiment of the present invention wherein a pair of capacitors are disposed in a plug of an electrosurgical hand piece.

As best illustrated in the cross-section drawing of FIG. 17, relatively small axial capacitors 500 easily fit into the existing connector. However, larger capacitors would impact the available spacing of the mechanical assembly. FIG. 17 illustrates an embodiment of the present invention wherein a pair of 0.22 µF capacitors are disposed within the existing sub-assembly of the return pad connector on the cable according to an embodiment of the present invention.

While the analysis used here is not equivalent to a full mechanical tolerance analysis in a computer aided drafting software program, it does appear that both the 0.22 µF and the 0.33 µF capacitors fit acceptably in the connector sub-assembly; with the better of the two being the 0.22 µF cap. The reason for this is that a smaller footprint in profile makes manual placement of the capacitor within the clam-shell parts easier at final assembly.

Given the similarities between the connection of the tested ESU and current connection designs of other manufacturers, there should be no need to significantly alter the techniques, fixtures, hand-tools and consumables used in the assembly of the return electrode connector on the cable assembly.

Note that both capacitors have alternating benefits; the 0.33 µF being best electrically, but worse mechanically and the 0.22 µF being worse electrically, but best mechanically. It may be possible to use the 0.22 µF cap, if its electrical tolerance is sufficiently within an acceptable operating range for the selected ESU return pad sensing circuit.

Tolerance values as stated earlier are most economically obtained at a ±20% value for both capacitors. A brief calculation shows what the expected limits of the configuration for the 0.22 µF capacitors in series across the return pad terminals would be. The calculation is laid out below and the limits can be seen to be 0.088 µF at the minimum and 0.132 µF at the maximum.

$$C_{1min} := 0.8 \cdot .22 \, \mu F \qquad C_{1max} := 1.2 \cdot .22 \, \mu F$$

$$C_{2min} := 0.8 \cdot .22 \, \mu F \qquad C_{2max} := 1.2 \cdot .22 \, \mu F$$

$$C_{seriesmin} := \frac{1}{\left(\frac{1}{C_{1min}} + \frac{1}{C_{2min}}\right)} \quad C_{seriesmin} = 0.088 \cdot \mu F$$

$$C_{seriesmax} := \frac{1}{\left(\frac{1}{C_{1max}} + \frac{1}{C_{2max}}\right)} \quad C_{seriesmax} = 0.132 \cdot \mu F$$

Line one of the table of FIG. 14 illustrates the combination of one, 0.1 µF, 50 Vdc metalized-film cap in series with one, 0.22 µF poly cap across the return pad terminals. During the test, the ESU response verified that even at the lower limits of tolerance for the 0.22 µF capacitor (−20%), acceptable console response was obtained.

In consideration of the 0.33 µF capacitor, it is worthy of note, that while it may be harder to install due to its size, it can still be installed, and so may provide results which are more desirable than that of the 0.22. µF capacitor.

The initial findings reveal that 0.22 µF and 0.33 µF ceramic, axial form-factor, capacitors, exist that are readily available from suppliers. Both Mechanical and electrical tolerances were examined, on a cursory level, to determine if further work in validating these options for use with ESUs is worthwhile.

Of particular interest are worst-case analyses of maximum power dissipation through exact form-factor capacitor examples recommended herein, to determine heating effects. Referring back to the basic explanation of capacitance, it can be seen that overall impedance is inversely proportional to frequency of output signal. Thus, higher frequencies will have less heating effects and lower frequencies will have greater heating effects. This, of course, is dependent on output signal architecture of the particular ESU.

Figure 18:
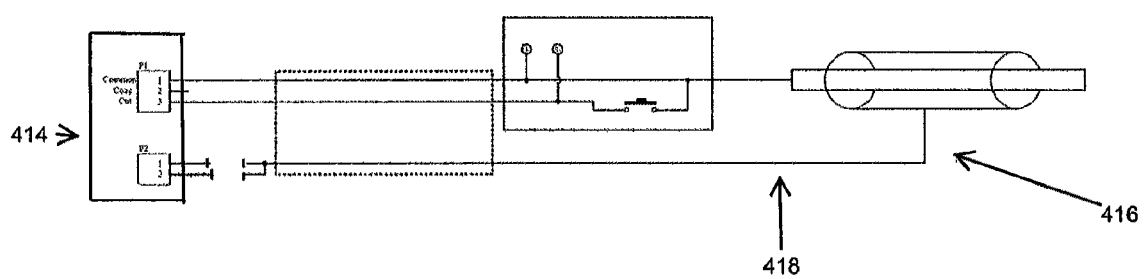
FIG. 18 schematically illustrates a bipolar electrosurgical hand piece connected to a monopolar output of an ESU according to an embodiment of the present invention.

No tooling or general assembly technique changes appear necessary during manufacturing of the various components of the various embodiments of the present invention in order to implement embodiments of the invention. FIG. 18 is schematically illustrates a bipolar electrosurgical hand piece connected to a monopolar output of an ESU in accordance with the teachings of an embodiment of the present invention.

Calculations:
Series Capacitance Quick Calc:

$$C_1 := .33 \, \mu F \qquad C_2 := .33 \, \mu F$$

$$C_{2series} := \frac{1}{\left(\frac{1}{C_1} + \frac{1}{C_2}\right)} \quad C_{2paratot} := C_1 + C_2$$

$$C_{2series} = 0.165 \cdot \mu F \quad C_{2paratot} = 0.66 \cdot \mu F$$

For a typical tolerance of +/−20%, such as that found on the DigiKey Website for these capacitors, the resulting capacitance would work out to be (at Min./Max. limits):

$$C_{1min} := 0.8 \cdot .22 \, \mu F \qquad C_{1max} := 1.2 \cdot .22 \, \mu F$$

$$C_{2min} := 0.8 \cdot .22 \, \mu F \qquad C_{2max} := 1.2 \cdot .22 \, \mu F$$

-continued $$C_{seriesmin} := \frac{1}{\left(\frac{1}{C_{1min}} + \frac{1}{C_{2min}}\right)} \quad C_{seriesmin} = 0.088 \cdot \mu F$$

$$C_{seriesmax} := \frac{1}{\left(\frac{1}{C_{1max}} + \frac{1}{C_{2max}}\right)} \quad C_{seriesmax} = 0.132 \cdot \mu F$$

$$C_{paramin} := C_{1min} + C_{2min} \quad C_{paramin} = 0.352 \cdot \mu F$$

$$C_{paramax} := C_{1max} + C_{2max} \quad C_{paramax} = 0.528 \cdot \mu F$$

Series Capacitance target Calc. for assembling a series analog close to 0.08 µF (min.):

$$C_{1lowtol} := .2 \; \mu F$$

$$C_{2lowtol} := .1 \; \mu F$$

$$C_{2seriesLT} := \frac{1}{\left(\frac{1}{C_{1lowtol}} + \frac{1}{C_{2lowtol}}\right)}$$

$$C_{2seriesLT} = 0.067 \cdot \mu F$$

The preceding examples can be repeated with similar success by substituting the generically or specifically described components and/or operating conditions of embodiments of the present invention for those used in the preceding examples.

Although the description above contains many specific examples, these should not be construed as limiting the scope of the invention but merely providing illustrations of some of the presently preferred embodiments of this invention. For example, monopolar to bipolar bridge circuitry can be combined or otherwise coupled, with additional power inputs to provide DC current sensing tools for either an integrated or stand-alone monitoring system of the treatment site characteristics.

Thus the scope of the invention should be determined by the appended claims and their legal equivalents, rather than narrowed by the specific illustrative examples given.

Although the invention has been described in detail with particular reference to described embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An adaptor comprising:
an adaptor input which at least substantially mates with a monopolar output of an electrosurgical generator;
a second adaptor input which at least substantially mates with a monopolar return input of the electrosurgical generator;
two adaptor outputs which at least substantially mate with a bipolar device piece;
an electrical component connected with the adaptor such that when the electrosurgical generator powers the bipolar device piece through the adaptor output:
the bipolar device piece receives an unaltered monopolar output RF signal produced from the monopolar output of the electrosurgical generator; and
the electrosurgical generator observes a bipolar return signal from the bipolar device piece at the monopolar return input, wherein the bipolar return signal from the bipolar device piece is configured to fall within a programmed predetermined safety impedance range of the electrosurgical generator such that the bipolar return signal is substantially the same as a monopolar return signal observed by the electrosurgical generator when the electrosurgical generator powers a monopolar device piece from the monopolar output and the monopolar return signal passes from the monopolar device piece to the monopolar return input of the electrosurgical generator through a return pad.

2. The adaptor of claim 1 wherein the electrical component comprises a capacitor.

3. The adaptor of claim 1 wherein the electrical component comprises a capacitor having a value of from about 0.05 pF to about 0.5 pF.

4. The adaptor of claim 1 wherein the at least one active electrical component comprises a capacitor having a value of from about 0.1 pF to about 0.33 pF.

5. The adaptor of claim 1 wherein the bipolar device piece is a bipolar hand piece.

6. The adaptor of claim 1 wherein the electrical component is selected from the group consisting of a capacitor, inductor, resistor, op-amp, fuse and combinations thereof.

* * * * *